(12) United States Patent
Alaswad

(10) Patent No.: US 10,307,575 B2
(45) Date of Patent: Jun. 4, 2019

(54) ANTEGRADE HEMODYNAMIC SUPPORT

(71) Applicant: Henry Ford Health System, Detroit, MI (US)

(72) Inventor: Khaldoon Alaswad, Pleasant Ridge, MI (US)

(73) Assignee: Henry Ford Health System, Detroit, MI (US)

( * ) Notice: Subject to any disclaimer, the term of this patent is extended or adjusted under 35 U.S.C. 154(b) by 0 days.

(21) Appl. No.: 15/943,477

(22) Filed: Apr. 2, 2018

(65) Prior Publication Data

US 2018/0280668 A1    Oct. 4, 2018

Related U.S. Application Data

(60) Provisional application No. 62/520,365, filed on Jun. 15, 2017, provisional application No. 62/481,024, filed on Apr. 3, 2017.

(51) Int. Cl.
| | |
|---|---|
| *A61N 1/362* | (2006.01) |
| *A61M 27/00* | (2006.01) |
| *A61M 1/10* | (2006.01) |
| *A61M 1/12* | (2006.01) |
| *A61M 25/00* | (2006.01) |
| *A61M 25/04* | (2006.01) |
| *A61M 25/09* | (2006.01) |

(Continued)

(52) U.S. Cl.
CPC .......... *A61M 27/002* (2013.01); *A61M 1/101* (2013.01); *A61M 1/1008* (2014.02); *A61M 1/122* (2014.02); *A61M 1/125* (2014.02); *A61M 1/10* (2013.01); *A61M 1/1698* (2013.01); *A61M 25/003* (2013.01); *A61M 25/04* (2013.01); *A61M 25/0668* (2013.01); *A61M 25/09041* (2013.01); *A61M 2025/0031* (2013.01)

(58) Field of Classification Search
CPC ...... A61M 1/10; A61M 1/1008; A61M 1/101; A61M 1/122; A61M 1/125; A61M 1/1698; A61M 2025/0031; A61M 25/003; A61M 25/04; A61M 25/0668; A61M 25/09041; A61M 27/002
See application file for complete search history.

(56) References Cited

U.S. PATENT DOCUMENTS

| | | |
|---|---|---|
| 5,965,089 A | 10/1999 | Jarvik et al. |
| 6,673,041 B1 | 1/2004 | Macoviak |

(Continued)

OTHER PUBLICATIONS

"International Application Serial No. PCT/US2018/025718, International Search Report dated Jun. 28, 2018", 2 pgs.

(Continued)

*Primary Examiner* — George Manuel
(74) *Attorney, Agent, or Firm* — Schwegman Lundberg & Woessner, P.A.

(57) ABSTRACT

The procedure to place antegrade hemodynamic support (AHS) combine currently available procedures and devices in a unique fashion to solve a significant problem for patients who need large bore hemodynamic support. The AHS procedure involves delivering an AHS device or a catheter connected to an AHS device to a patient's aorta in an antegrade fashion, alleviating the workload on the patient's heart and supporting the patient hemodynamically to maintain normal functions of the body organs.

20 Claims, 39 Drawing Sheets

(51) Int. Cl.
A61M 1/16 (2006.01)
A61M 25/06 (2006.01)

(56) References Cited

U.S. PATENT DOCUMENTS

| | | |
|---|---|---|
| 2002/0013571 A1 | 1/2002 | Goldfarb et al. |
| 2008/0076959 A1 | 3/2008 | Farnan et al. |
| 2009/0112050 A1 | 4/2009 | Farnan et al. |
| 2009/0149950 A1* | 6/2009 | Wampler .............. A61M 1/101 623/3.13 |
| 2016/0082176 A1 | 3/2016 | Kelly et al. |

OTHER PUBLICATIONS

"International Application Serial No. PCT/US2018/025718, Written Opinion dated Jun. 28, 2018", 7 pgs.

* cited by examiner

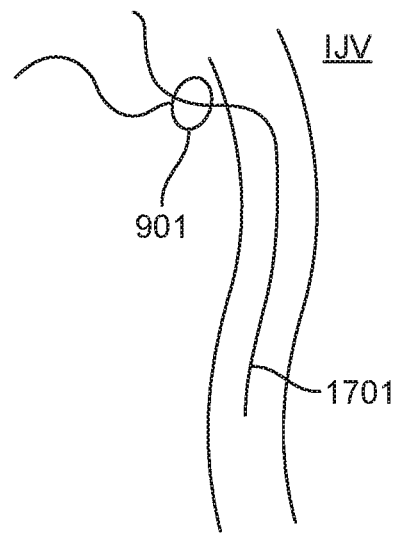
FIG. 19
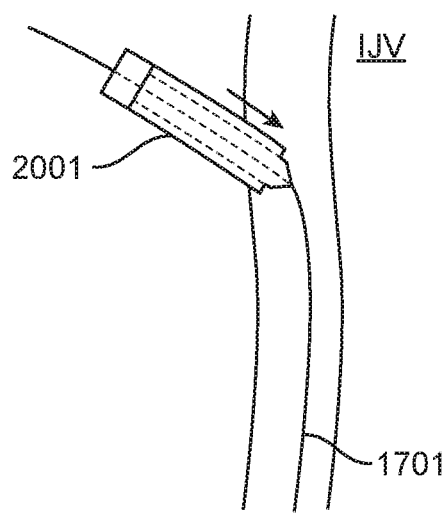 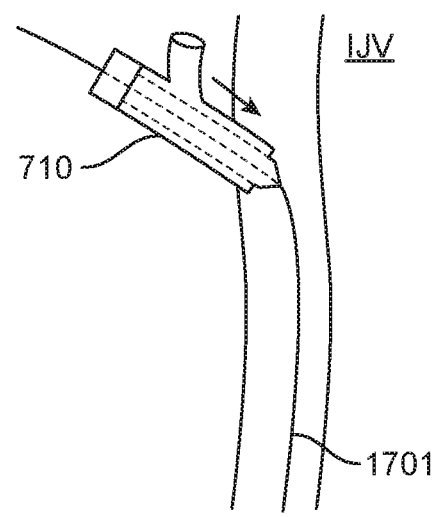
FIG. 20              FIG. 21

ANTEGRADE HEMODYNAMIC SUPPORT

RELATED APPLICATIONS

This application claims the benefit of U.S. Provisional Patent Application No. 62/520,365 filed on Jun. 15, 2017, and U.S. Provisional Patent Application No. 62/481,024 filed on Apr. 3, 2017, each incorporated herein by reference in its entirety.

BACKGROUND OF THE INVENTION

Patients who need hemodynamic support with currently available devices for left ventricular failure require large bore arterial access. The arterial access is obtained either surgically or percutaneously by advancing a needle in an artery, threading a guidewire through the needle, and then advancing large catheters over the wire into the arterial system.

SUMMARY OF THE INVENTION

Clinical trials have demonstrated up to 40% access site complications during hemodynamic support. Most of these complications happen as a result of the large bore arterial access. Additionally, successful access to the arterial vasculature may be affected by other vascular diseases. Also arterial access is typically accomplished at the patient's groin which affects patient mobility. Therefore it would be desirable to provide improved methods and systems for hemodynamic support that overcome at least some of the challenges with the arterial access site. The antegrade hemodynamic support can replace all percutaneous and surgical ventricular assist devices.

The present invention generally relates to medical systems, devices and methods, and more particularly relates to methods and systems of providing hemodynamic support to a patient's heart.

In embodiments of the present subject matter, methods and systems related to providing hemodynamic support to a patient's heart for alleviating workload therefrom are provided. In a first aspect, a method comprises providing a hemodynamic support system and a catheter. The catheter comprises at least two lumens, an inlet port, and an outlet port, which is distal of the inlet port. The method further comprises introducing the catheter into a vein of the patient and advancing the catheter in an antegrade direction into a vena cava. The catheter is also advanced into a right atrium and passed transseptally from the right atrium into a left atrium. The catheter is also advanced across a mitral valve, through a left ventricular outflow tract, and into an aorta. The catheter removes blood from the patient via the inlet port and through a first of the at least two lumens and delivers the blood to another portion of the hemodynamic support system. The catheter also returns the blood to the patient through a second of the at least two lumens to the aorta through the outlet port, which is adjacent a distal portion of the catheter. The method alleviates the workload on the patient's heart. The method may also support the patient's normal body functions. The method may be used in combination with or substituted with any catheter, catheter system, hemodynamic support device, guide wire, snare, hemodynamic support system, or any other method of providing hemodynamic support to a patient described herein.

Optionally, the method may introduce a guide wire into the vein, over which a catheter may advance. The method may optionally introduce a catheter into any vein of the patient, which includes, but is not limited to, a common femoral vein or an internal jugular vein or subclavian vein, which permits increased patient mobility. The method may optionally advance the catheter into the ascending aorta. The method may also optionally be performed without large bore arterial access or be provided to a patient having peripheral artery disease. The method may optionally comprise delivering the blood to a portion of the hemodynamic support system that is a pump. These methods may also be optionally used in combination with or substituted with any catheter, catheter system, hemodynamic support device, guide wire, snare, hemodynamic support system, or any other method of providing hemodynamic support to a patient described herein.

In a second aspect, a method of delivering hemodynamic support to a patient's heart for alleviating workload therefrom comprises providing a hemodynamic support system with an outer catheter and an inner catheter. The outer catheter, which has at least three ports, is introduced into a vein of the patient and advanced towards the heart. The inner catheter, which has an outlet port disposed on a distal portion thereof, is introduced into a first port of the outer catheter. The inner catheter is advanced through the outer catheter in an antegrade direction and exits out a third port, which is disposed on a distal portion of the outer catheter. The outlet port is disposed in an aorta. The outer catheter removes blood from the patient via the third port or a plurality of apertures disposed on the distal portion of the outer catheter to act as further inlets. The third port or the plurality of apertures is disposed anywhere proximal of the outlet port, which includes, but is not limited to, the vena cava, the right atrium, the left atrium, or the left ventricle. The outer catheter moves the blood through the second port and delivers the blood to another portion of the hemodynamic support system. The outlet port returns the blood to the patient. The method alleviates the workload on the patient's heart. The method may also support the patient's normal body functions. Optionally, in this or other embodiments, the catheters are made to resist kinking in the same time advanced around the heart with the largest lumen(s) possible in combination with the thinnest catheter walls possible. In some embodiments, the lumens have a diameter of any size, including but not limited to ⅜ inches, ⅘ inches, or larger or smaller diameters. Optionally, in this or other embodiments, the inner catheter or the outer catheter is precurved to sit in the heart without impinging on the heart structure and to facilitate delivery of the catheter. Optionally, in this or other embodiments, the catheter is made entirely of collapsible material or partially of collapsible material. This will facilitate the delivery of the catheter and the collapsible part of the catheter will expand upon pumping blood or fluid through it. Optionally, in this or other embodiments, the inner catheter can be in-forced longitudinally to prevent the catheter from collapsing back. The method may be used in combination with or substituted with any catheter, catheter system, hemodynamic support device, guide wire, snare, hemodynamic support system, or any other method of providing hemodynamic support to a patient described herein.

Optionally, the method may introduce a guide wire into the vein, over which the outer or inner catheter may advance. The method may also introduce the outer catheter or inner catheter into any vein of the patient, which includes, but is not limited to, a common femoral vein or an internal jugular vein, which permits increased patient mobility. The method may optionally comprise delivering the blood to a portion of the hemodynamic support system that is a pump. The method may also optionally include advancing the inner catheter in an antegrade direction. By way of example, this method of advancing in an antegrade fashion may include advancing the inner catheter into a vena cava, into a right atrium, passing the inner catheter transseptally from the right atrium into a left atrium, advancing the inner catheter across a mitral valve, and advancing the catheter through a left ventricular outflow into the aorta. The method may optionally include advancing the inner catheter into an ascending aorta. The method may also optionally be performed without large bore arterial access or be provided to a patient having peripheral artery disease. The method may optionally include a Y-shape at a proximal end of the outer catheter formed by the first and second port. The method may also optionally include having a plurality of apertures be circumferentially disposed around the distal portion of the outer catheter. The method may also optionally include having a plurality of axially oriented elongate elements, which may further optionally comprise of a plurality of radially expandable elements that forms a barrier around the third port or the plurality of apertures to prevent tissue from obstructing the port or aperture, disposed along the distal portion of the outer catheter. The plurality of radially expandable elements may further optionally form an anchor for the outer catheter. The method may also optionally have a plurality of radially expandable elements be self-expanding. The method may optionally have a plurality of radially expandable elements extend radially outward from the distal end of the outer catheter, curve towards the proximal portion of the outer catheter, and connect with the outer catheter at a location proximal to the distal end. The method may optionally have the plurality of radially expandable elements extend radially outward and past the distal end of the outer catheter, curve towards the proximal portion of the outer catheter, and connect with the outer catheter at a location proximal to the distal end. The method may also optionally include having the distal portion of the outer catheter be flared to form a trumpet shape. Optionally, in this or other embodiments, the expanded elements at the distal end of the catheter fix the catheter in place and prevent the migration of the catheter to different locations within the circulation. Optionally, in this or other embodiments, the expanded elements help prevent the cardiac tissues from collapsing over the inlet port and obstructing the blood flow. These methods may be also optionally used in combination with or substituted with any catheter, catheter system, hemodynamic support device, guide wire, snare, hemodynamic support system, or any other method of providing hemodynamic support to a patient described herein.

In a third aspect, a method of delivering hemodynamic support to a patient's heart for alleviating workload therefrom comprises providing a hemodynamic support device. The hemodynamic support device is introduced into a vein of the patient and advanced in an antegrade direction into the heart by advancing into a vena cava, into a right atrium, passing transseptally into the left atrium, across a mitral valve, through a left ventricular outflow tract and into an aorta. The hemodynamic support device operates and applies a treatment to blood in the aorta by pumping the blood into the circulation. The method alleviates the workload on the patient's heart. The method may also support the patient's normal body functions. The method may be used in combination with or substituted with any catheter, catheter system, hemodynamic support device, guide wire, snare, hemodynamic support system, or any other method of providing hemodynamic support to a patient described herein.

Optionally, the method may introduce a guide wire into the vein, over which the hemodynamic support device may advance. The method may also introduce the hemodynamic support device into any vein of the patient, which includes, but is not limited to, a common femoral vein or an internal jugular vein. The method may optionally advance the hemodynamic support device into the ascending aorta. The method may optionally also be performed without large bore arterial access or be provided to a patient having peripheral artery disease. The method may optionally be performed with hemodynamic support devices including, but not limited to, ventricular assist devices, extra corporeal membrane oxygenator systems, modified or unmodified percutaneously insertable temporary ventricular support devices, modified or unmodified percutaneous heart pump, or intra-aortic balloon pumps. The method may optionally have the hemodynamic support device be operated by introducing blood disposed in the left atrium or the left ventricle into an inlet port of the hemodynamic support device. The method may further have multiple inlet ports in the left atrium or the left ventricle. The method may optionally have the treatment to blood in the aorta comprise of pumping blood disposed in the left atrium or the left ventricle directly into the aorta. In some embodiments, the hemodynamic support device may comprise a catheter, an inlet port, an outlet port, and a pump, wherein a distal portion of the catheter is disposed in the aorta. Optionally, the pump is disposed internally within the catheter. In further embodiments, the pump may be disposed in the left ventricle, mitral valve, or left atrium. These methods may be also optionally used in combination with or substituted with any catheter, catheter system, hemodynamic support device, guide wire, snare, hemodynamic support system, or any other method of providing hemodynamic support to a patient described herein.

In the next aspect, a method of delivering hemodynamic support to a patient's heart for alleviating workload therefrom comprises providing a hemodynamic support system comprising a catheter system, a second catheter, a snare, and a guide wire. The snare is introduced into an internal jugular vein of the patient and advanced into an inferior vena cava. A second catheter is introduced into a common femoral vein of the patient and advanced through the open loop of the snare. The second catheter is advanced in an antegrade fashion into a right atrium, passed transseptally into the right atrium into the left atrium, across a mitral valve, through a left ventricular outflow tract into an aorta. A guide wire is introduced into the second catheter from the common femoral vein and advanced to the aorta. The second catheter is removed from the patient while the guide wire remains in the patient. The snare snares the guide wire and externalizes a proximal portion of the guide wire from the internal jugular vein or the subclavian vein. A catheter system is introduced into the internal jugular vein or the subclavian vein and advanced into the heart. A distal portion of the catheter system is positioned in the aorta. In some embodiments, the method may skip the snaring in the inferior vena cava and establish the transseptal puncture from the neck or subclavian vein. The method may be used in combination with or substituted with any catheter, catheter system, hemodynamic support device, guide wire, snare, hemodynamic support system, or any other method of providing hemodynamic support to a patient described herein.

Optionally, the method may further comprise a second snare, which may be introduced into any artery of the patient, which may include, but is not limited to, common femoral artery, radial artery, brachial artery, or an axillary artery. The method may optionally have the second snare one end of the guide wire near the aorta the left ventricle or the left atria. The method may further have the option of externalizing the end snared by the second snare from any artery, including externalized from a peripheral artery. The method may further be optionally used with any catheter, catheter system, hemodynamic support device, hemodynamic support system, guide wire, snare, or any other method of providing hemodynamic support to a patient described herein or any combination thereof. By way of example, the method may optionally include having the catheter system comprise a catheter having at least two lumens, an outlet port, and an inlet port, which is proximal of the outlet port. The method may further have the option of advancing a portion of the aforementioned catheter system in an antegrade direction into a vena cava, into a right atrium, passing transseptally into a left atrium, across a mitral valve, through the left ventricular outflow tract, and into an aorta. The method may also optionally have this catheter system remove blood from the patient via the inlet port and through a first of the at least two lumens and deliver the blood to another portion of the hemodynamic support system. The method may also optionally have this catheter system returns the blood to the patient through a second of the at least two lumens to the aorta through the outlet port, which is adjacent a distal portion of the catheter. This method may also optionally alleviate the workload on the patient's heart. The method may also support the patient's normal body functions. This method may optionally comprise delivering the blood to a portion of the hemodynamic support system that is a pump. In another example, the method may optionally include having the catheter system comprise an outer catheter and an inner catheter. This method may optionally include having the outer catheter, which has at least three ports, be introduced into a vein of the patient and advanced towards the heart. This method may also optionally include the inner catheter, which has an outlet port disposed on a distal portion thereof, be introduced into a first port of the outer catheter. This method optionally may have the inner catheter advance through the outer catheter in an antegrade direction and exit out a third port, which is disposed on a distal portion of the outer catheter. This method may also optionally have the outlet port be disposed in an aorta. This method may further have the option to have the outer catheter remove blood from the patient via the third port or a plurality of apertures disposed on the distal portion of the outer catheter. This method may optionally also have the third port or the plurality of apertures be disposed anywhere proximal of the outlet port, which includes, but is not limited to, the vena cava, the right atrium, the left atrium, or the left ventricle. The outer catheter may optionally move the blood through the second port and deliver the blood to another portion of the hemodynamic support system. This method may optionally have the outlet port return the blood to the patient. This method may optionally alleviate the workload on the patient's heart. The method may also support the patient's normal body functions. In another example, the method may optionally include having the catheter system comprise two separate catheters, an inlet catheter and an outlet catheter. The inlet catheter may also optionally comprise an inlet port disposed on a distal portion thereof. The outlet catheter may also optionally comprise an outlet port disposed on a distal portion thereof. The outlet catheter may optionally be introduced into a vein of the patient and advanced in an antegrade direction into an aorta. The outlet port may also be optionally disposed in the aorta. The inlet catheter also may be optionally introduced into a vein of the patient and advanced proximal to the outlet port. In some embodiments, the inlet catheter optionally removes blood from the patient via the inlet port and delivers the blood to another portion of the hemodynamic support system. Optionally, in this or other embodiments, the entire or only the portion of the outlet catheter that runs to a lower ventricular outflow tract into the ascending aorta may be made of collapsible material, for example polytetrafluoroethylene (PTFE), that expands with the fluid pumping into the catheter. Optionally, in this or other embodiments, the outlet catheter can be in-forced longitudinally to prevent the catheter from collapsing back. Optionally, in this or other embodiments, the outlet catheter can have a balloon at the tip to facilitate floating with the blood flow to the aorta. The collapsible outlet catheter will prevent the catheter from impinging on the heart structures like the mitral valve. The distal end of the outlet catheter might be delivered to the ascending aorta by snaring the tip in the venous system, the RA, the LA, or the LV. Optionally, in this or other embodiments, the inlet catheter can be made of rubber plastic or PTFE with a dilator for delivery. The lumen of this inlet catheter may optionally be configured to maximize flow rate. The lumen could also in some embodiments be 4 to 10 mm, but not limited to these dimensions. Optionally, in this and other embodiments, the outlet catheter could be entirely or partially be made of PTFE. Optionally, in this and other embodiments, the outlet catheter could be with or without metal wires enhancement longitudinally. Optionally, in this and other embodiments, the outlet catheter could be delivered over a soft dilator, or be collapsed inside a smaller diameter peel away sheath/catheter that can be peeled away after it facilitates the delivery of the collapsed outlet catheter. Optionally, in this and other embodiments, the outlet and inlet catheter could have proximal adapter to facilitate attachment to the pump or deliver the catheters in a concentric fashion, where the outlet catheter slides inside the inlet catheter from a different port. The method may be also optionally used in combination with or substituted with any catheter, catheter system, hemodynamic support device, guide wire, snare, hemodynamic support system, or any other method of providing hemodynamic support to a patient described herein.

In another aspect, a catheter system for providing hemodynamic support to a patient comprises an outer catheter and an inner catheter. The outer catheter comprises at least three ports. The inner catheter comprises an outlet port disposed on a distal portion thereof. The first and second ports of the outer catheter are disposed at a proximal portion of the outer catheter. The first port is configured to receive the inner catheter and the second port is configured to move blood from a patient to a portion of a hemodynamic support system. The inner catheter is disposed in the outer catheter through the first port and passes through the third port disposed on a distal portion thereof. The third port is proximal of the outlet port and is configured to remove blood from the patient. The outlet port is configured to return the blood to the patient. The system may be used in combination with or substituted with any catheter, catheter system, hemodynamic support device, guide wire, snare, hemodynamic support system, or any other method of providing hemodynamic support to a patient described herein.

Optionally, the catheter system has a plurality of apertures to act as further inlets on the outer catheter configured to remove blood from the patient. The catheter system may optionally have the first and second port form a Y-shape. The catheter system may optionally have the plurality of apertures be circumferentially disposed around the distal portion of the outer catheter. The catheter system may also have the option to have a plurality of axially oriented elongate elements, which may further optionally comprise of a plurality of radially expandable elements that forms a barrier around the third port or the plurality of apertures to prevent tissue from obstructing the port or aperture, disposed along the distal portion of the outer catheter. The plurality of radially expandable elements may further optionally form an anchor for the outer catheter. The catheter system may also optionally have a plurality of radially expandable elements be self-expanding. The catheter system may optionally have a plurality of radially expandable elements extend radially outward from the distal end of the outer catheter, curve towards the proximal portion of the outer catheter, and connect with the outer catheter at a location proximal to the distal end. The catheter system may optionally have the plurality of radially expandable elements extend radially outward and past the distal end of the outer catheter, curve towards the proximal portion of the outer catheter, and connect with the outer catheter at a location proximal to the distal end. The catheter system may also optionally include having the distal portion of the outer catheter be flared to form a trumpet shape. The system may be also optionally used in combination with or substituted with any catheter, catheter system, hemodynamic support device, guide wire, snare, hemodynamic support system, or any other method of providing hemodynamic support to a patient described herein.

In a different aspect, a method of providing hemodynamic support to a patient's heart for alleviating workload therefrom comprises providing a hemodynamic support system. The hemodynamic support system comprises two separate catheters, an inlet catheter and an outlet catheter. The inlet catheter may optionally comprise an inlet port disposed on a distal portion thereof. The outlet catheter may optionally comprise an outlet port disposed on a distal portion thereof. The outlet catheter may be introduced into a vein of the patient and advanced in an antegrade direction into an aorta. The outlet port may be disposed in the aorta. The inlet catheter also may be introduced into a vein of the patient and advanced proximal to the outlet port. In some embodiments, the inlet catheter removes blood from the patient via the inlet port and delivers the blood to another portion of the hemodynamic support system. In further embodiments, the outlet catheter returns the blood to the patient by delivering the blood to the aorta via the outlet port. The method alleviates the workload on the patient's heart. The method may also support the patient's normal body functions. The method may be used in combination with or substituted with any catheter, catheter system, hemodynamic support device, guide wire, snare, hemodynamic support system, or any other method of providing hemodynamic support to a patient described herein.

Optionally, the introduction of the inlet or outlet catheter into the vein of the patient may optionally comprise introducing a guide wire into the vein and advancing either the inlet or outlet catheters over the guide wire. The introduction of the inlet or outlet catheters may further optionally comprise accessing the common femoral vein or introducing either catheter into an internal jugular vein or a subclavian vein, thereby permitting increased patient mobility. In some embodiments, the outlet catheter may be advanced in an antegrade direction into an ascending aorta. In further embodiments, the outlet catheter may be advanced in an antegrade direction into an aorta by advancing the outlet catheter in an antegrade direction into a vena cava, into a right atrium, passing the outlet catheter transseptally from the right atrium into a left atrium, advancing the outlet catheter across a mitral valve, and advancing the outlet catheter through a left ventricle outflow tract into the aorta. Optionally, the inlet port may be disposed in the left atrium, left ventricle, mitral valve, anywhere in the venous system, anywhere in the right heart (including, but not limited to the right atrium, tricuspid valve, or the right ventricle), or in the pulmonary artery. The inlet catheter may optionally have a plurality of apertures disposed on the catheter. In some embodiments, the plurality of apertures may be circumferentially disposed around the distal portion of the inlet catheter. In further embodiments, the plurality of apertures may be disposed throughout the entire inlet catheter. In other embodiments, the inlet catheter may optionally comprise a plurality of axially oriented elongate elements disposed along the distal portion of the inlet catheter, whereby the plurality of elongate elements radially expand to form a barrier around the inlet port or the plurality of apertures to prevent tissue from obstructing the inlet port or the plurality of apertures. The plurality of radially expandable elements may further optionally form an anchor for the inlet catheter. The distal portion of the inlet catheter may optionally be flared to form a trumpet shape. The plurality of radially expandable elements may optionally be self-expanding. The plurality of radially expandable elements may optionally extend radially outward from the distal end of the inlet catheter, curve towards the proximal portion of the inlet catheter, and connect with the inlet catheter at a location proximal to the distal end. In other embodiments, the plurality of radially expandable elements may also optionally extend radially outward and past the distal end of the inlet catheter, curve towards, the proximal portion of the inlet catheter, and connect with the inlet catheter at a location proximal to the distal end. Optionally, removing blood from the patient through the inlet catheter may comprise removing unoxygenated blood from the right side of the heart or a vessel coupled to the right side of the heart. Optionally, the inlet and outlet catheters may be introduced into the same vein or into different veins. The method may also optionally be performed without large bore arterial access or be provided to a patient having peripheral artery disease. The method may optionally comprise delivering the blood to a portion of the hemodynamic support system that is a pump. In some embodiments, wherein the delivered blood is deoxygenated, the pump may comprise an extra corporeal oxygenator system for oxygenating the blood and removing the CO2 before the blood is returned to the patient. These methods may also be optionally used in combination with or substituted with any catheter, catheter system, hemodynamic support device, guide wire, snare, hemodynamic support system, or any other method of providing hemodynamic support to a patient described herein.

In another aspect, a system for providing hemodynamic support to a system comprising a sheath and a second catheter slideably disposed in the sheath is provided. Optionally, the distal tip of the second catheter may be disposed in the aorta. The sheath may be configured for arterial access or more preferably venous access to the heart in an antegrade fashion to introduce any catheter, catheter system, hemodynamic support device, guide wire, snare, hemodynamic support system, or any other method of providing hemodynamic support to a patient described herein. Optionally, the sheath can be configured in shapes that facilitate delivery of any catheter, catheter system, hemodynamic support device, guide wire, snare, hemodynamic support system, or any other method of providing hemodynamic support to any chamber of the heart or the circulatory system. Optionally, the sheath may be peel away sheath so it may be removed by peeling it away or other mechanism leaving behind any of the catheter, catheter system, hemodynamic support device, guide wire, snare, or hemodynamic support system described herein. The sheath comprises one or more proximal heads. The proximal head may optionally receive a catheter or other medical devices. The proximal head may optionally operatively couple the sheath with another device such as an external pump. The sheath may also comprise a distal tip. Optionally, the distal tip of the sheath may be advanced to or disposed in any part of the heart, the venous system, the arterial system, or the circulatory system, including the right atrium RA, right ventricle RV, left ventricle LV, or the aorta AO. Optionally, the blood may be removed from the sheath or returned to the second catheter. The sheath may also be optionally configured to remove blood from the heart. Optionally, the sheath can be used in replacement of an inlet or an aspiration catheter including any of those described herein. Optionally, the sheath may be introduced from the internal jugular vein IJV, the subclavian vein, or from any of the typical groin access points such as the femoral artery or the femoral vein. Optionally, the proximal head may have a valve such as a duckbill valve or Tuohy-Borst valve for sealing off the proximal end to prevent blood flow or air aeration past the proximal head. Optionally, the sheath is configured to operatively couple with another device. Optionally, the sheath may be further attached to an external pump.

In a final aspect, a catheter system for providing support to a patient comprises two separate catheters. The two catheters comprise an inlet catheter and an outlet catheter. The inlet catheter comprises an inlet port disposed on a distal portion thereof and the outlet catheter comprises an outlet port disposed on a distal portion thereof. The system may be also optionally used in combination with or substituted with any catheter, catheter system, hemodynamic support device, guide wire, snare, hemodynamic support system, or any other method of providing hemodynamic support to a patient described herein.

Optionally, the inlet catheter comprises a plurality of apertures disposed on the catheter. In some embodiments, the plurality of apertures may be circumferentially disposed around the distal portion of the inlet catheter. The plurality of apertures may also optionally be disposed throughout the entire inlet catheter. In some embodiments, the inlet catheter may comprise a plurality of axially oriented elongate elements disposed along the distal portion of the inlet catheter, wherein the plurality of elements is configured to radially expand to form a barrier around the inlet port or the plurality of apertures, the barrier configured to prevent tissue from obstructing the inlet port or the plurality of apertures. The plurality of radially expandable elements may further optionally form an anchor for the inlet catheter. The plurality of elements may take the form of a flared trumpet or a cage described in the specification earlier herein. In other embodiments, the plurality of radially expandable elements may be self-expanding. The system may be also optionally used in combination with or substituted with any catheter, catheter system, hemodynamic support device, guide wire, snare, hemodynamic support system, or any other method of providing hemodynamic support to a patient described herein. Optionally, in this catheter embodiment or any other catheter embodiment described herein, the catheter is made of one or more materials that is resistant to thrombosis or can be bound to anticoagulant like heparin. Optionally, in this and other embodiments, a catheter can have an additional lumen with a separate proximal port to infuse anticoagulant, any solution, or the patient's own blood into the cardiac chamber or the vasculature. This additional lumen may be useful to prevent clotting inside the cardiac chamber or the vasculature, and/or the catheter can be fenestrated to leak some of the pumped blood in the LA or the LV to prevent blood stagnation and thrombosis in the cardiac chambers or the ascending aorta and maintain the heart valves normal functions.

Optionally, in any embodiment, the method of antegrade delivery of a hemodynamic support system utilizing any catheter or catheter system to deliver antegrade hemodynamic support and passing a catheter or catheter system transseptally from the right atrium to the left atrium described herein may comprise of utilizing a peel away sheath to access the left atrium and subsequently delivering the inlet and outlet catheters in a concentric fashion, double lumen fashion, or two separate catheters fashion. Optionally, in any embodiment, the method of antegrade delivery of a hemodynamic support system comprising access from the internal jugular vein (IJV) or the subclavian vein may be performed without access to the common femoral artery. Optionally, in any embodiment, a guide wire may be externalized from any vein, but preferably from the internal jugular vein (IJV) or the subclavian vein, or possibly from a peripheral artery. Optionally, in any embodiment, the distal portion of a catheter (e.g., inner, outer, inlet, outlet, plurality of lumen, Y-shaped, or any catheter or catheter system described herein) may comprise a plurality of apertures along with a hole in the distal end of the catheter. Optionally, in any embodiment, the distal portion of a catheter (e.g., inner, outer, inlet, outlet, plurality of lumen, Y-shaped, or any catheter or catheter system described herein) does not comprise a plurality of apertures aside from a hole in the distal end of the catheter.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 19 illustrates an exemplary embodiment of the snare in FIG. 9 externalizing a proximal portion of the guide wire in FIG. 17 from the internal jugular vein.

FIG. 20 illustrates an exemplary embodiment of a catheter advancing over the guide wire in FIG. 17 from the internal jugular vein.

FIG. 21 illustrates an exemplary embodiment of the catheter in FIG. 7 advancing through the guide wire in FIG. 17 from the internal jugular vein.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Historically, patients who need hemodynamic support with the currently available devices for left ventricular failure require large bore arterial access. The arterial access is obtained either surgically or percutaneously by advancing a needle in an artery, threading a guidewire through the needle, and then advancing a catheter over the guidewire into the arterial system. Clinical trials have demonstrated up to 40% access site complications during hemodynamic support. Access complications may be the Achilles heel of percutaneous hemodynamic support. Currently, patients with severe peripheral artery disease have very limited options that are still associated with significant risk to the patient similar problems arise if the patient has small arteries.

Hemodynamic support device placement through a vein to access the ascending aorta has not been performed before. Providing hemodynamic support through an antegrade fashion, i.e., in the direction of blood flow where freshly oxygenated blood moves away from the heart toward the brain, provides numerous advantages. Avoidance of large bore arterial access will significantly decrease the bleeding complications and possibly death. Antegrade hemodynamic support also expands the indication for hemodynamic support to patients with peripheral artery disease or small arteries. Antegrade hemodynamic support also provides co-axial blood flow to the head and the coronary arteries first, which may have advantages over the retrograde flow offered by devices such as extra corporeal membrane oxygenation (ECMO) and circulatory support devices such as the TandemHeart™. Moreover, as many patients with hemodynamic support devices may be bed-bound, antegrade hemodynamic support from an internal jugular vein access or other vein will increase patient mobility, including sitting in a chair or walking. Further, the venous access provides a room to place a larger diameter outflow catheter, which will provide a larger flow capacity and increased support. In turn, this increased support can, in some embodiments, totally replace the cardiac function. In addition to providing additional physiologic antegrade flow, the disclosed antegrade hemodynamic support would provide better unloading of the left ventricle, which would allow for better left ventricle recovery. Antegrade hemodynamic support could alleviate a patient heart's workload, and provide hemodynamic support to sustain normal function of the body organs. Using large bore catheters will allow using the pump at a lower speed, which will decrease the damage to the blood elements and decrease hemolysis.

Figure 1:
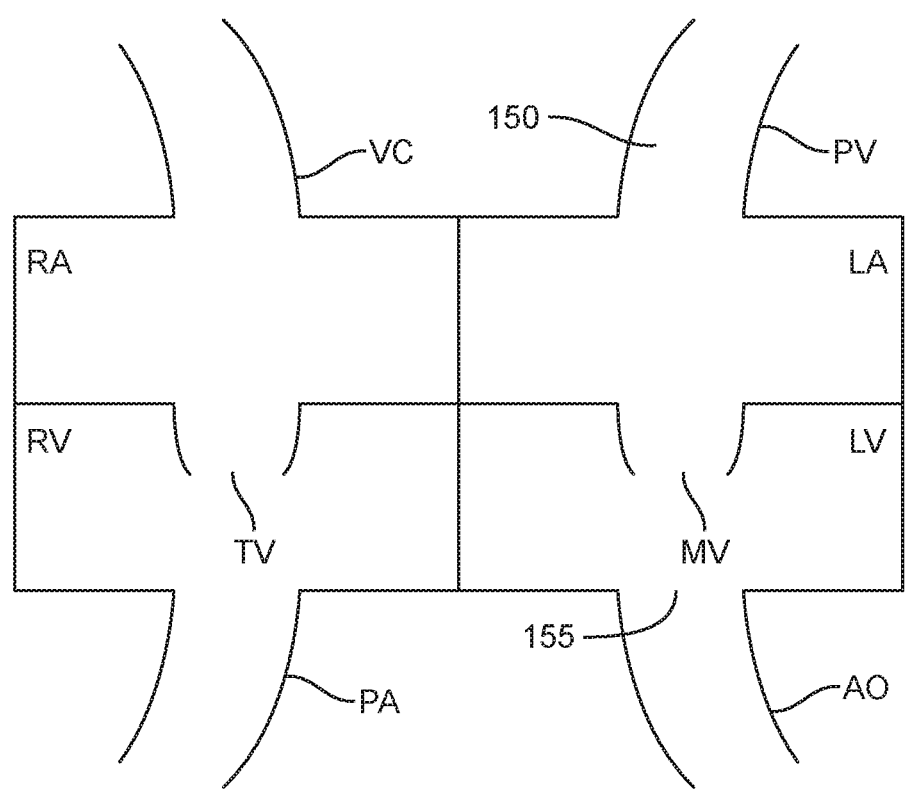
FIG. 1 shows a schematic diagram of basic human heart anatomy.

FIG. 1 shows a schematic diagram of basic human heart anatomy. FIG. 1 portrays the four chambers, the right atrium RA right ventricle RV, left atrium LA, and left ventricle LV. FIG. 1 also depicts the tricuspid valve TV, which is between the right atrium RA and right ventricle RV, and the mitral valve MV, which is between the left atrium LA and left ventricle LV. FIG. 1 further illustrates four major blood vessels, the vena cava VC, which brings deoxygenated blood, i.e., blood not yet oxygenated by the lungs, from the head and body to the right atrium RA, the pulmonary artery PA, which delivers unoxygenated blood out of the right ventricle RV to the lungs, the pulmonary vein PV, which brings oxygenated blood from the lungs to the left atrium LA, and the aorta AO, which delivers oxygenated blood to the rest of the body. FIG. 1 also portrays where the pulmonary valve 150 and aortic valve 155 are located.

Figure 2A:
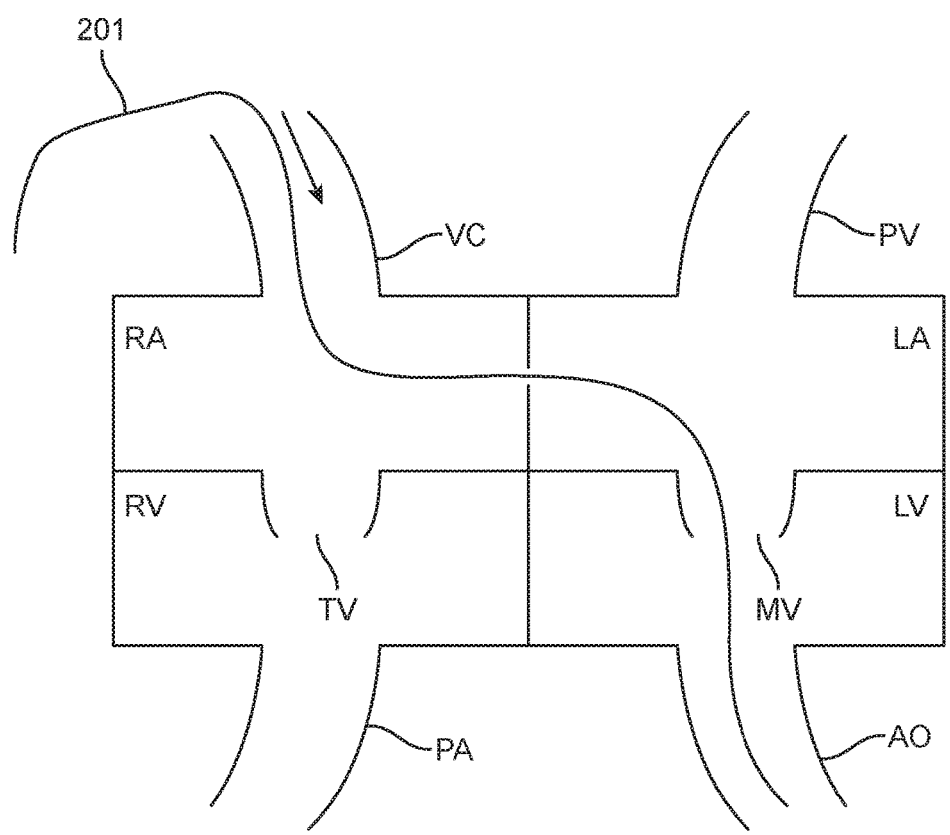
FIG. 2A illustrates an exemplary embodiment of a guide wire advancing through the heart in FIG. 1 and into the aorta in an antegrade fashion.

FIGS. 2A-2F illustrate an exemplary embodiment of a hemodynamic support system advancing through the heart of a patient in an antegrade fashion. A guide wire 201 in FIG. 2A is inserted in a vein to act as a guide for a catheter that is part of a hemodynamic support system to rapidly follow for easier delivery to a site. The guide wire is advanced into the right atrium, then transseptally into the left atrium, across the mitral valve into the left ventricle, and then out the left ventricular outflow tract into the aorta. Optionally, the guide wire diameter can range from 0.009 inches to 0.063 inches, and lengths can range up to 300 cm or more. However, one of skill in the art will appreciate that the length of guide wire is not limited to the aforementioned range and that any guide wire length may be used depending on the kind of procedure or measurements of the patient. In other embodiments the introduction of the hemodynamic support device into the vein comprises introducing the guide wire into an internal jugular vein or a common femoral vein. However, one of skill in the art will appreciate that the kind of veins the guide wire or hemodynamic support system may be introduced into is not limited to just the aforementioned veins and that the hemodynamic support device may be introduced into any type of vein. Non-limiting examples of veins include, but are not limited to: a common femoral vein, an iliac vein, an antecubital vein, an axillary vein, a subclavian vein, a jugular vein, or a temporal vein. This method of advancing the hemodynamic support system may be used with any of the other methods or systems described therein and further may be used in combination with or substituted with any catheter, catheter system, hemodynamic support device, guide wire, snare, hemodynamic support system, or any other method of providing hemodynamic support to a patient described herein.

Figure 2B:
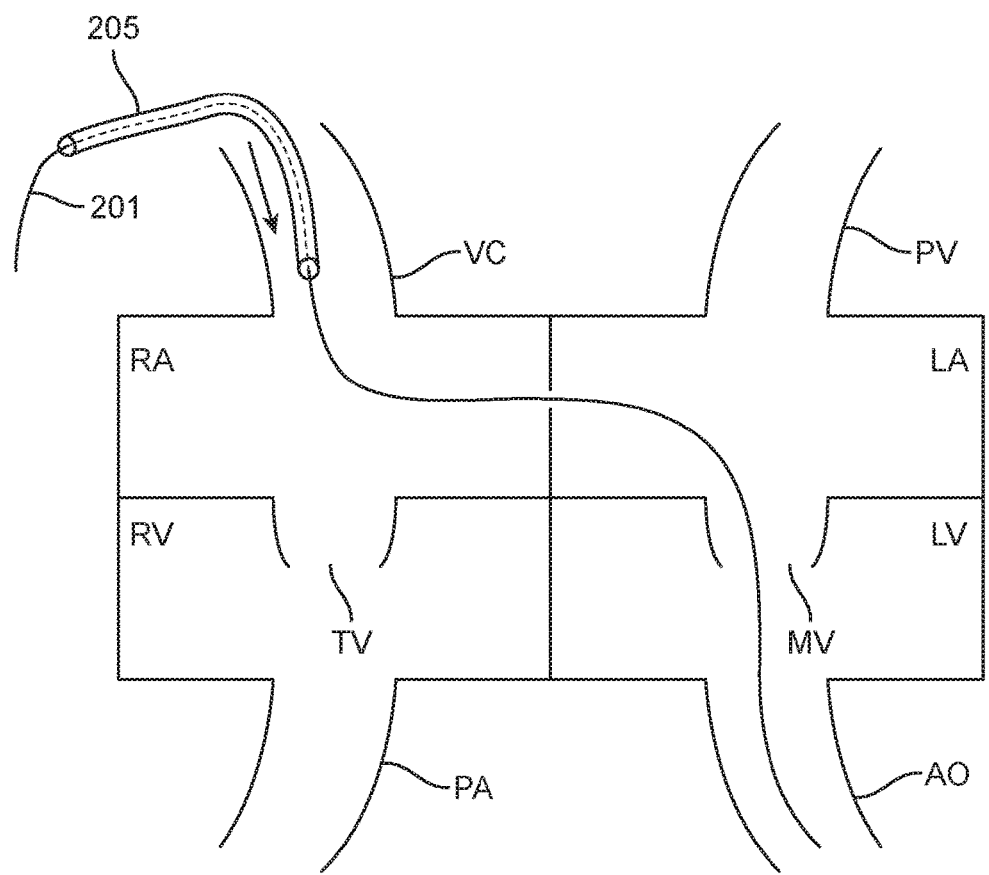
FIGS. 2B-2F illustrate an exemplary embodiment of a catheter from a hemodynamic support system advancing through the vena cava, through the right atrium, transseptally into the left atrium, across the mitral valve, through the left ventricle, and into the aorta in FIG. 1 in an antegrade fashion.
Figure 2C:
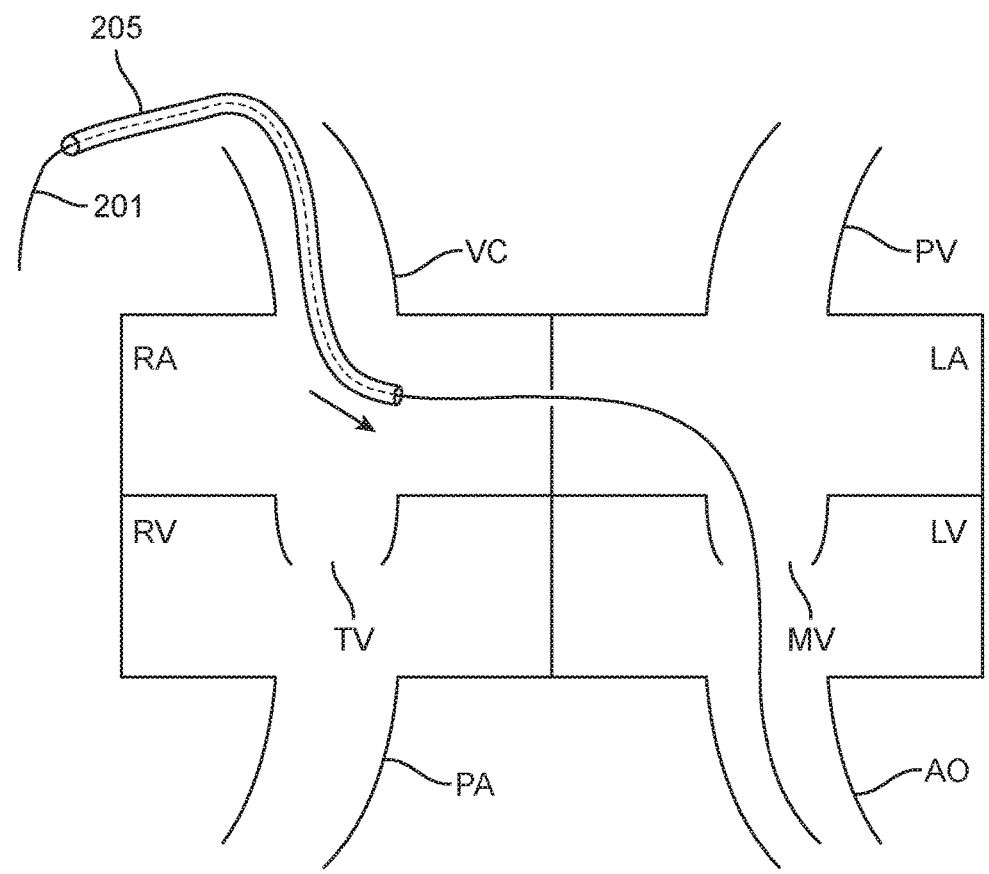
Figure 2D:
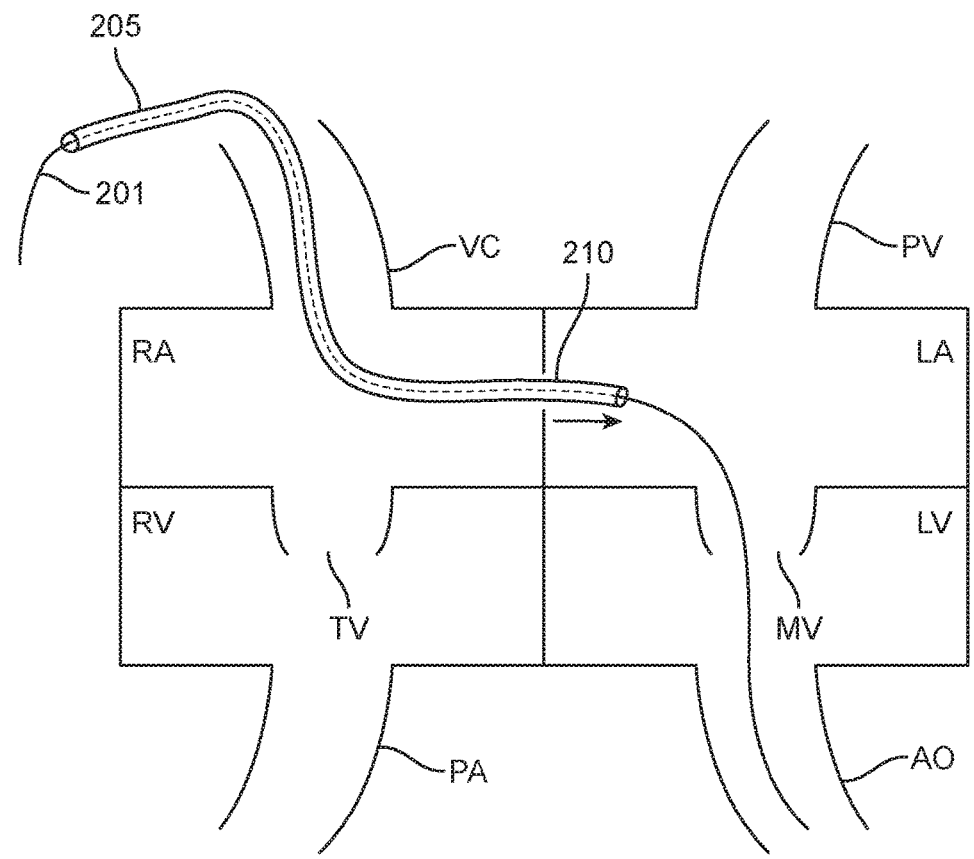
Figure 2E:
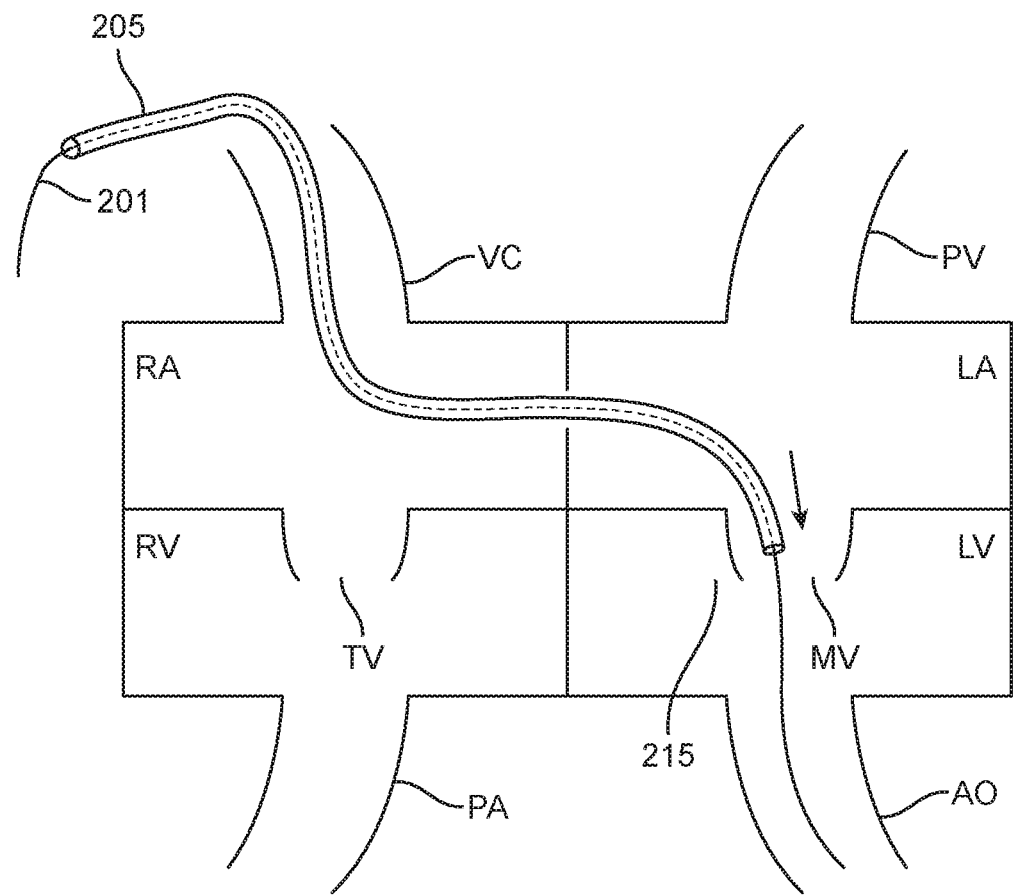
Figure 2F:
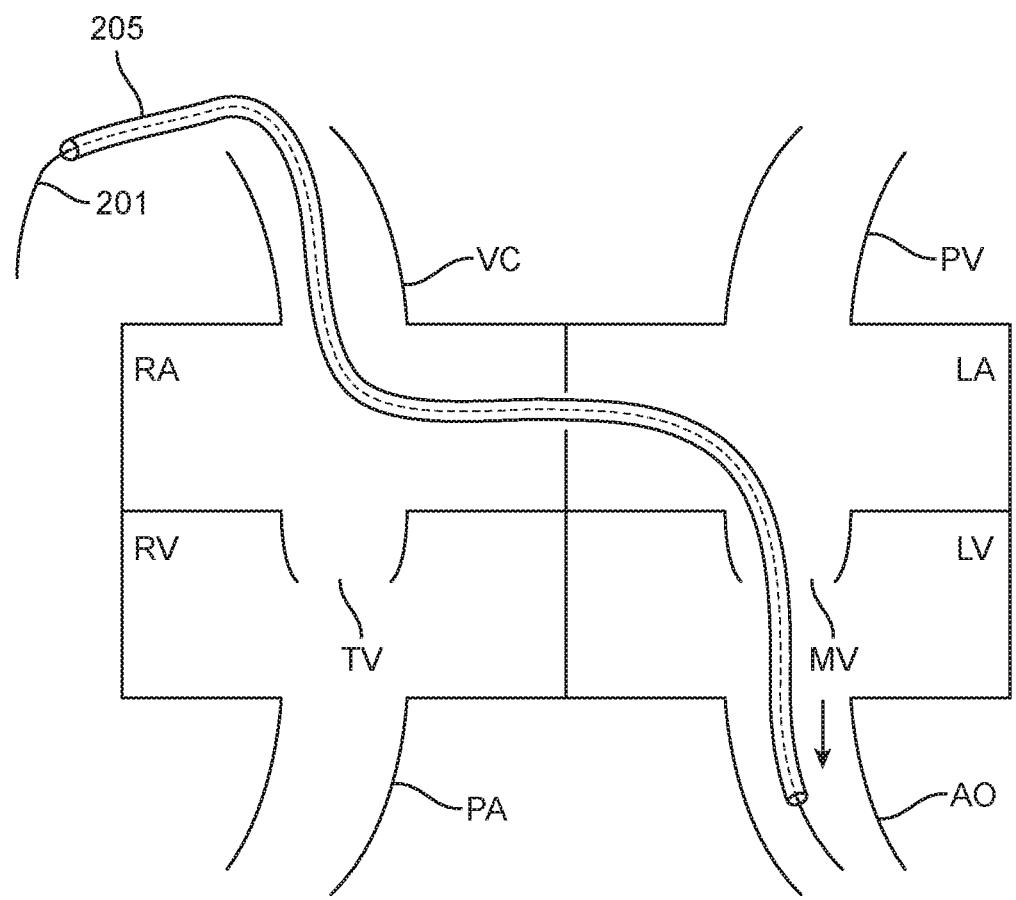

FIG. 2B depicts a part of the hemodynamic system including a catheter 205 advancing over the guide wire 201 to reach the vena cava VC in an antegrade fashion. FIG. 2C shows the catheter 205 further advancing into the right atrium RA in an antegrade fashion. FIG. 2D shows the catheter 205 accessing the left atrium LA via atrial-transseptal access 210 in an antegrade fashion using techniques known in the art to cross the septal wall. FIG. 2E shows the catheter 205 further advancing across the mitral valve MV in an antegrade fashion toward the left ventricular outflow tract 215. FIG. 2F shows the catheter 205 advancing into the ascending aorta AO. Once the catheter is disposed in the ascending aorta AO, hemodynamic support treatment may be applied to the patient. The catheter 205 comprises at least two lumens having an inlet port and an outlet port. The inlet port is proximal of the outlet port. The inlet port may optionally remove blood from the patient and through a first of the at least two lumens and deliver the blood to another portion of the hemodynamic support system such as a pump. Optionally, the blood may be returned to the patient by delivering the blood through a second of the at least two lumens, wherein the blood is returned from the outlet port to the aorta. The outlet port may optionally be adjacent a distal portion of the catheter. Non-limiting examples of where the inlet port can be located include: the vena cava VC, the right atrium RA, the left atrium LA, or the left ventricle LV. In instances where the inlet port is disposed in areas of the heart where the surrounding blood is not yet oxygenated from the lungs, e.g., vena cava VC or right atrium RA, the blood may be delivered to another portion of the hemodynamic support system that also oxygenates the delivered blood such as with an extra corporeal membrane oxygenation (ECMO) system. In instances where the inlet port is disposed in areas of the heart where the surrounding blood has already been oxygenated from the lungs, e.g., left atrium LA or left ventricle LV, the blood may be delivered to another portion of the hemodynamic support system without the oxygenation. The method of providing hemodynamic support may optionally be done without large bore arterial access. The method of providing hemodynamic support may optionally be performed on patients having peripheral artery disease or small arteries where arterial access would otherwise be challenging.

Optionally, a hemodynamic support device may be introduced into the vein of the patient and advanced in an antegrade fashion into the heart. One of skill in the art will appreciate that a variety of hemodynamic support devices may be used, including, but not limited to, ventricular assist devices, extra corporeal membrane oxygenation (ECMO) systems, or intra-aortic balloon pumps. Optionally, the introduction of the hemodynamic support device into the vein may comprise introducing a guide wire into the vein and advancing the hemodynamic support device over the guide wire. The guide wire diameter may optionally range from 0.009 inches to 0.063 inches. Guide wire length can be 300 cm or more. However, one of skill in the art will appreciate that the length of guide wire is not limited to the aforementioned range and that any guide wire length may be used depending on the kind of procedure or measurements of the patient. The introduction of the hemodynamic support device or guide wire into the vein may optionally comprise accessing and introducing the catheters and related equipment into an internal jugular vein, an axillary vein, a subclavian vein, or a common femoral vein. However, one of skill in the art will appreciate that the kind of veins the guide wire or hemodynamic support device may be introduced into is not limited to just the aforementioned veins and that they may be introduced into any type of vein. Non-limiting examples of veins include, but are not limited to: a common femoral vein, an iliac vein, an antecubital vein, an axillary vein, a subclavian vein, a jugular vein, or a temporal vein. Optionally, the hemodynamic support device may be advanced into the heart in an antegrade fashion whereby the hemodynamic support device is advanced in an antegrade direction into the vena cava; advanced in the antegrade direction into the right atrium; and advancing across the mitral valve, through the left ventricular outflow tract, and into the aorta in the antegrade direction. Optionally in this exemplary method or any other method the hemodynamic support device is operated and applies a treatment to blood in the aorta to alleviate the workload on the patient's heart. Optionally, the method of providing the hemodynamic device in an antegrade fashion is done without large bore arterial access. The method of providing hemodynamic device in an antegrade fashion may optionally be done to patients having peripheral artery disease or small arteries.

Figure 3:
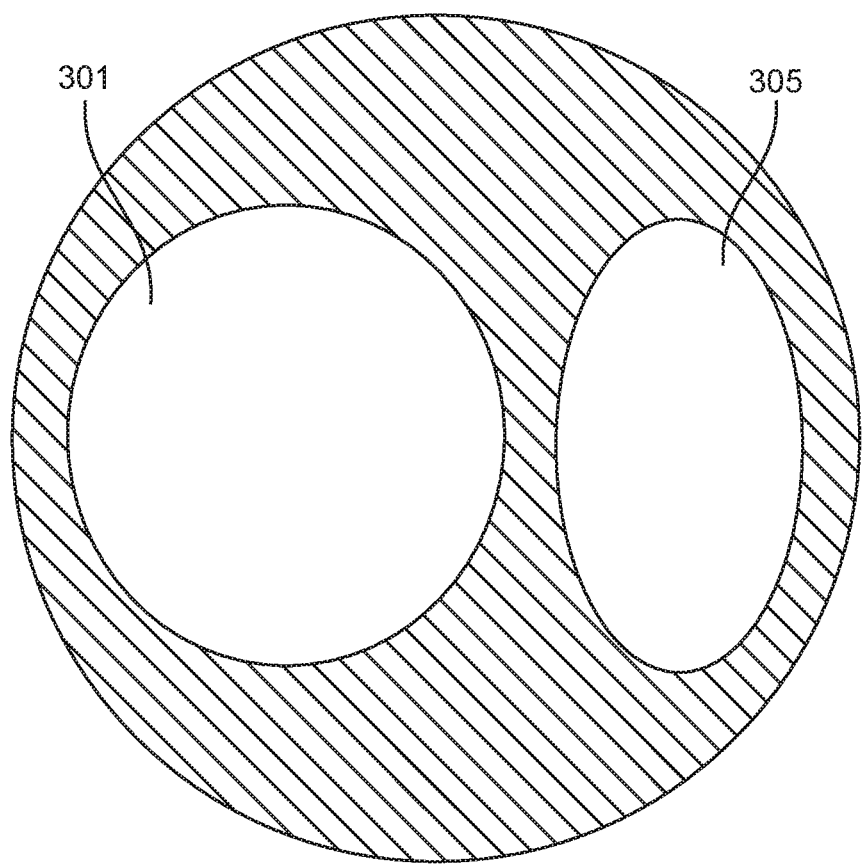
FIGS. 3-4 illustrate exemplary embodiments of a cross-section of a catheter from a hemodynamic support system.
Figure 4:
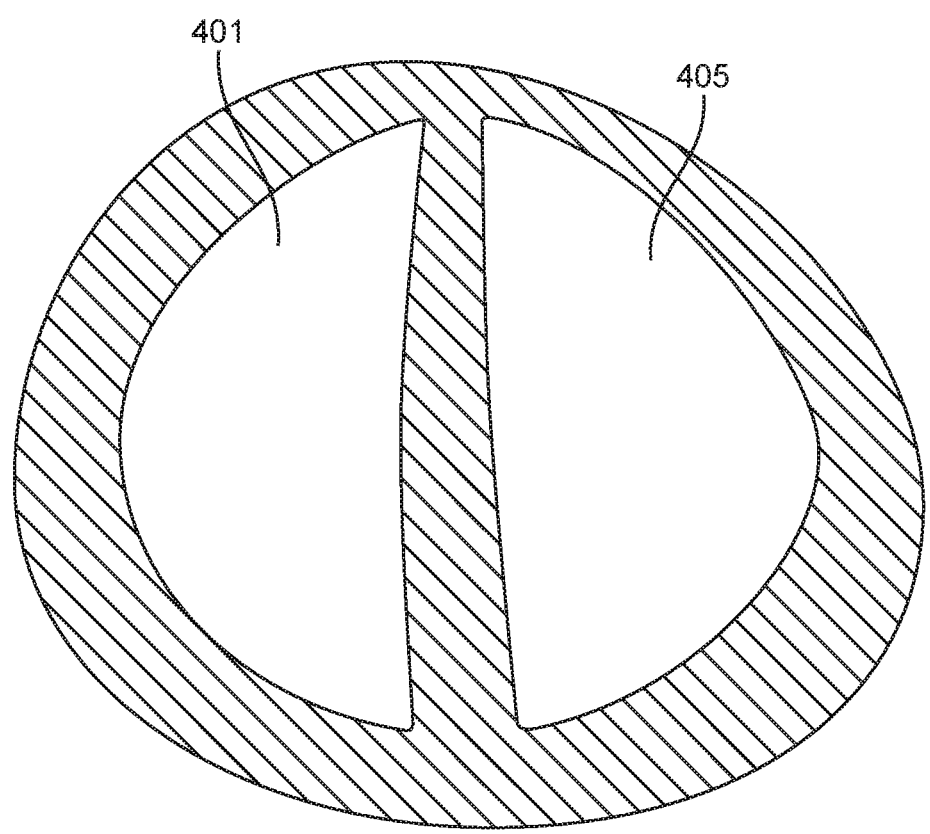
Figure 5:
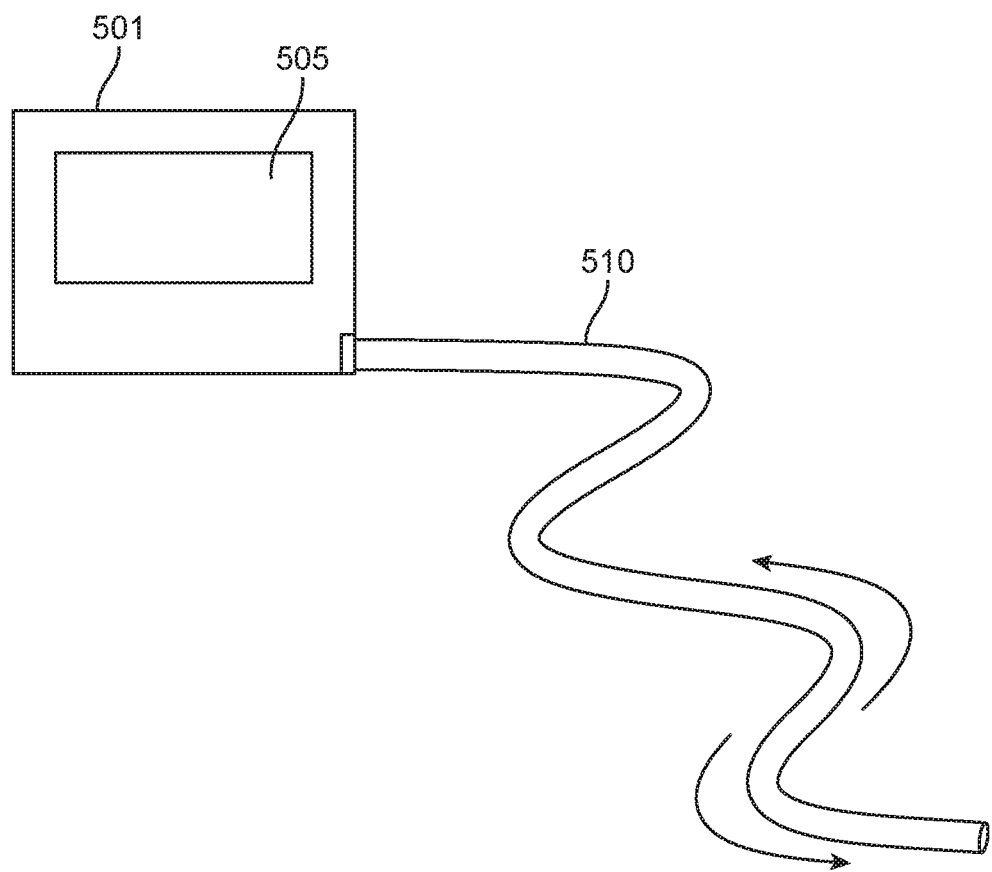
FIG. 5 illustrates an exemplary embodiment of a hemodynamic support system.
Figure 6A:
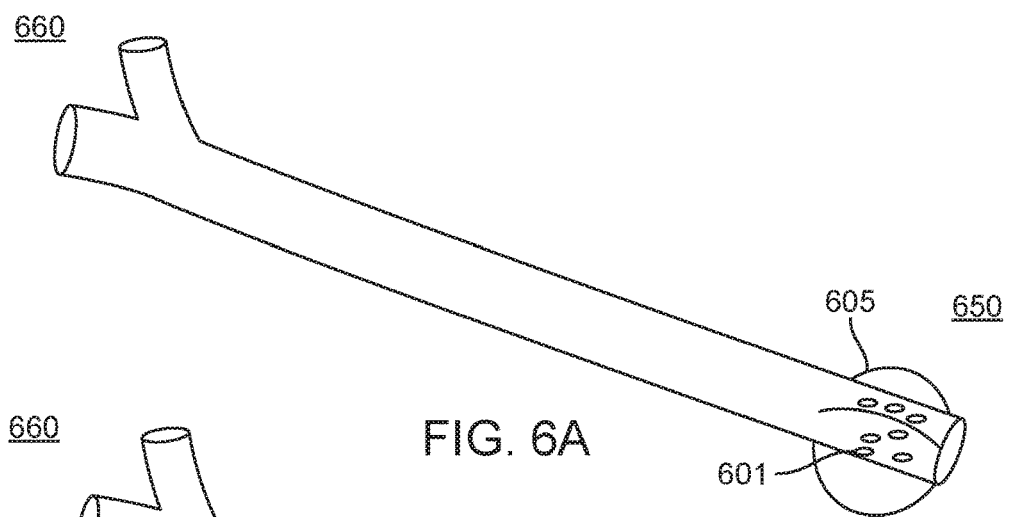
FIGS. 6A-6D illustrate exemplary embodiments of a catheter with three ports and different configurations in the distal portion of the catheter.
Figure 6B:
Figure 6C:
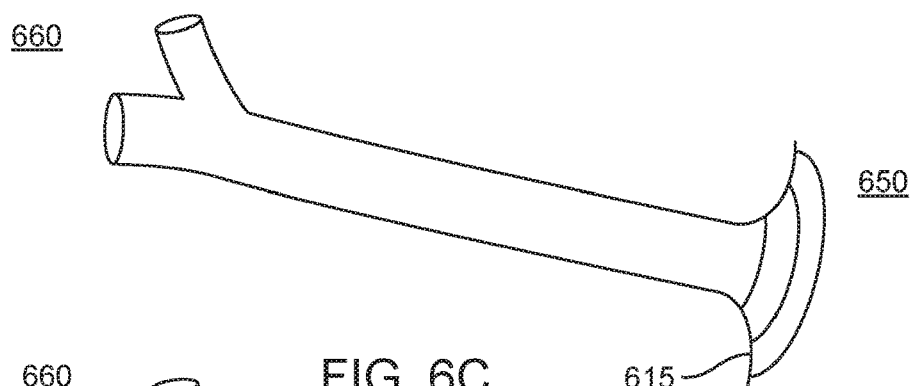
Figure 6D:
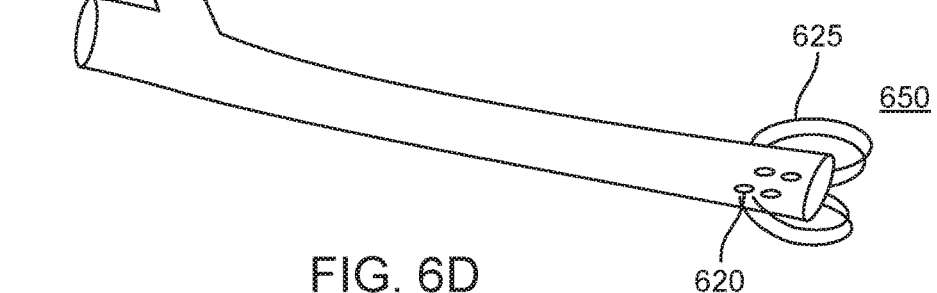
Figure 7:
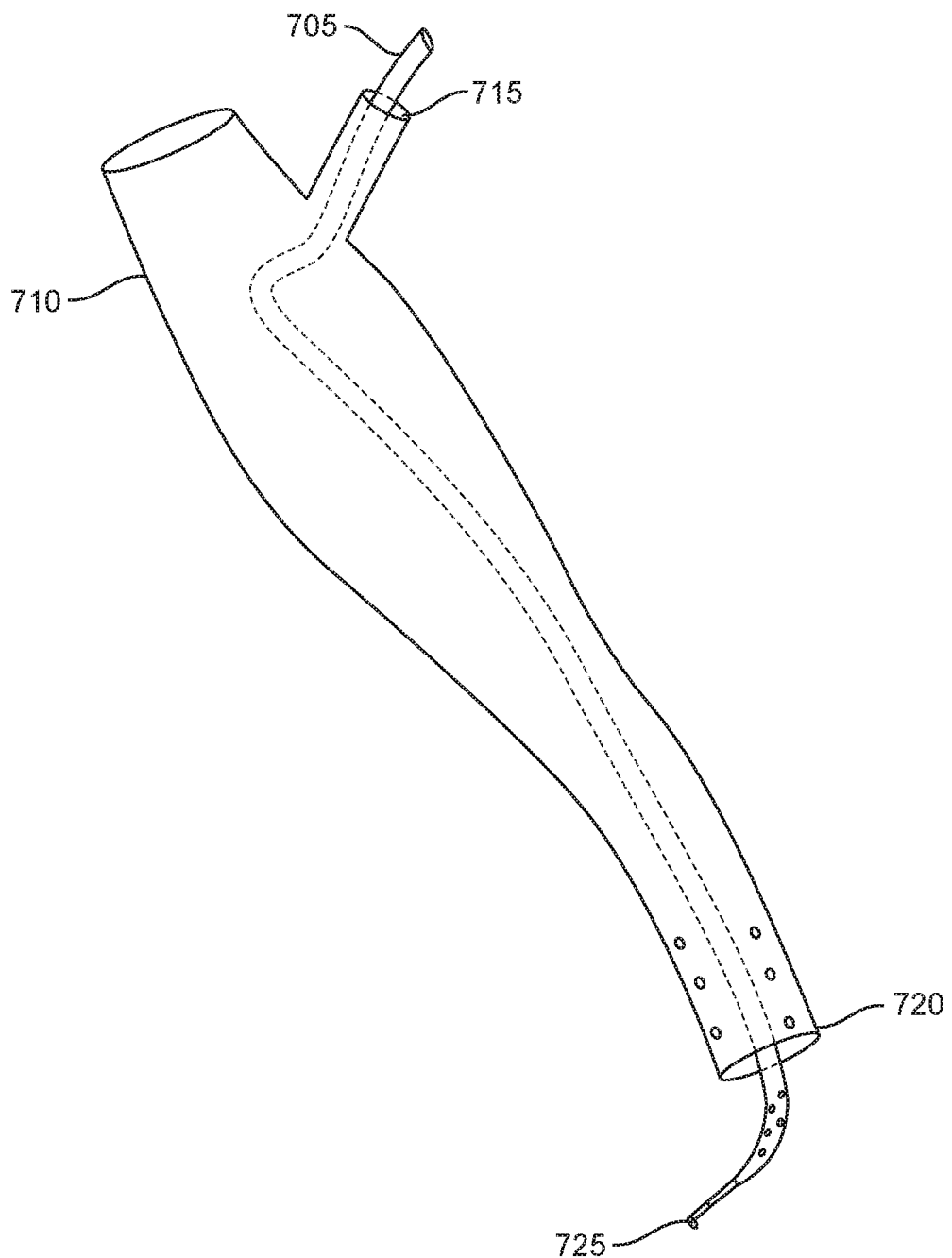
FIG. 7 illustrates an exemplary embodiment of an inner catheter disposed in an outer catheter with three ports.
Figure 8A:
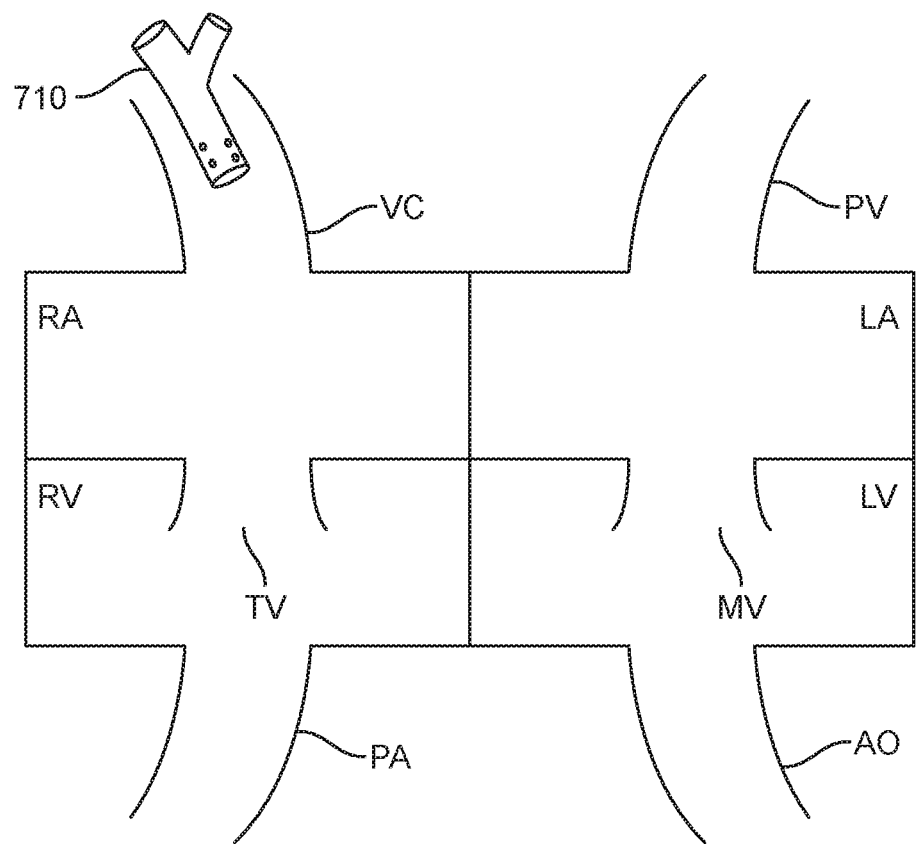
FIGS. 8A-8E illustrate an exemplary embodiment of the inner and outer catheters in FIG. 7 advancing in the heart in an antegrade fashion where the distal portion of the outer catheter is disposed in the vena cava and the distal portion of the inner catheter is disposed in the aorta.
Figure 8B:
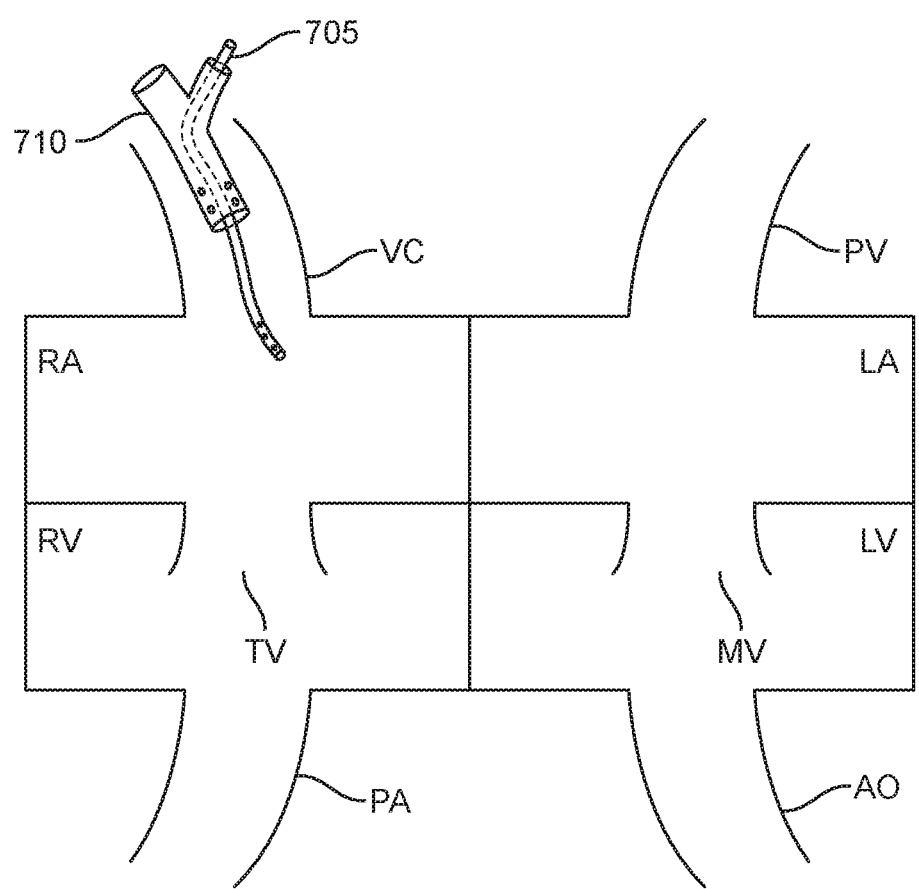
Figure 8C:
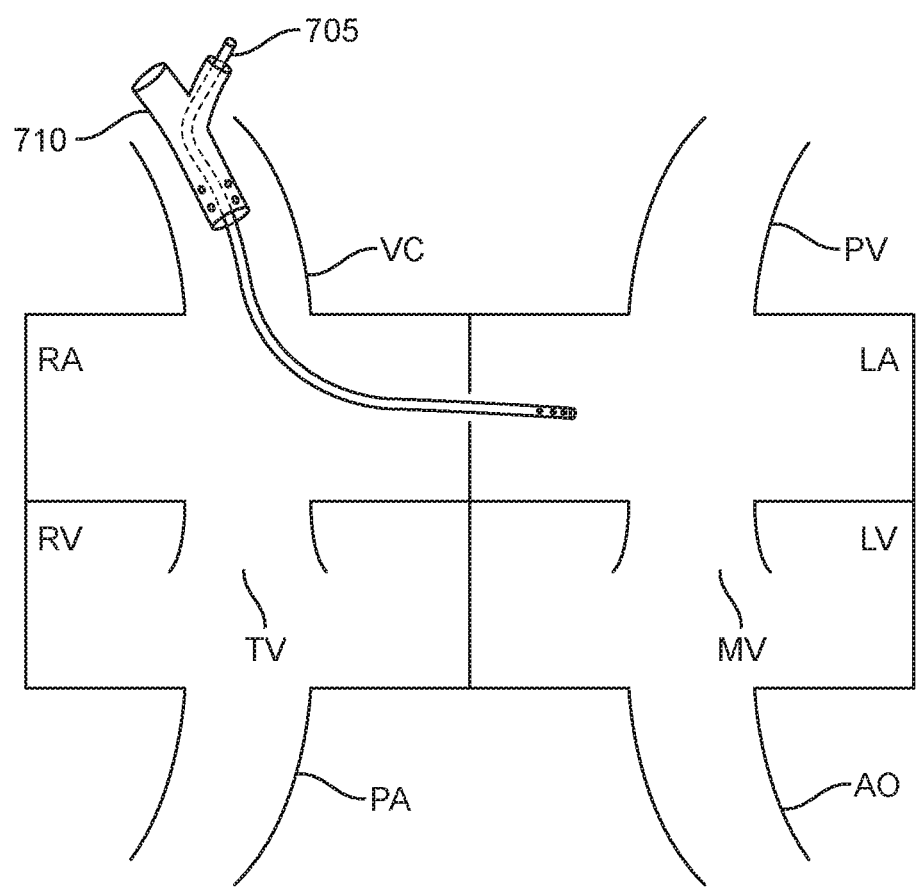
Figure 8D:
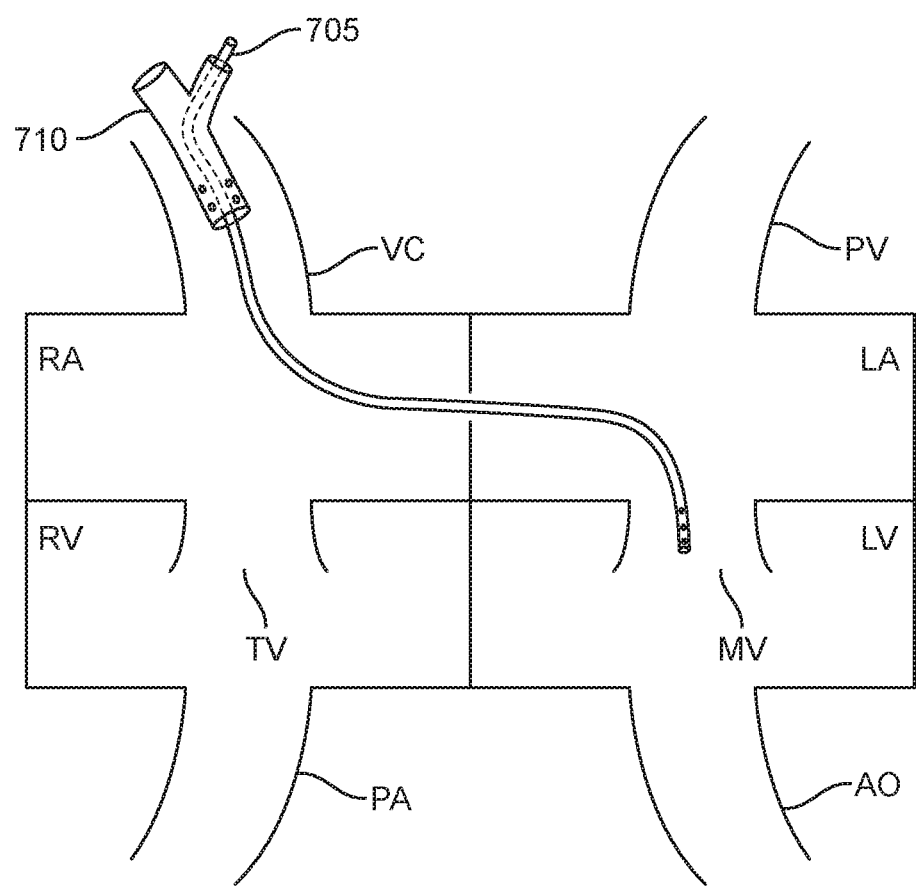
Figure 8E:
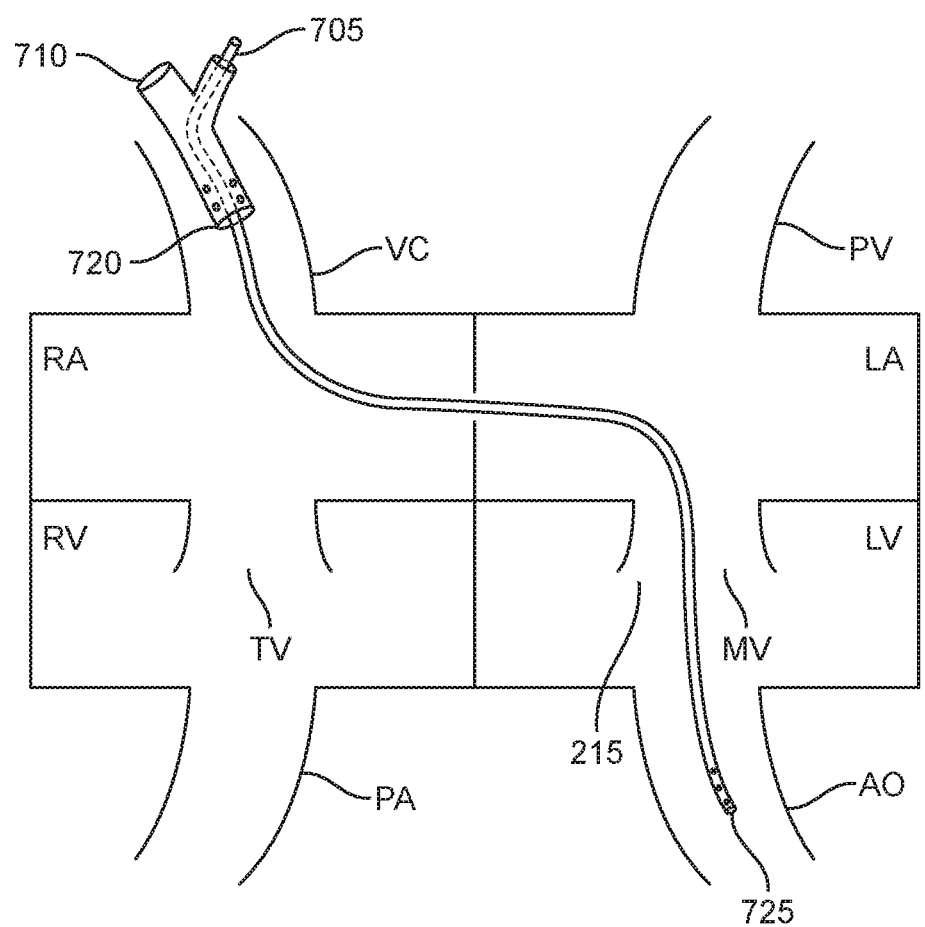
Figure 9:
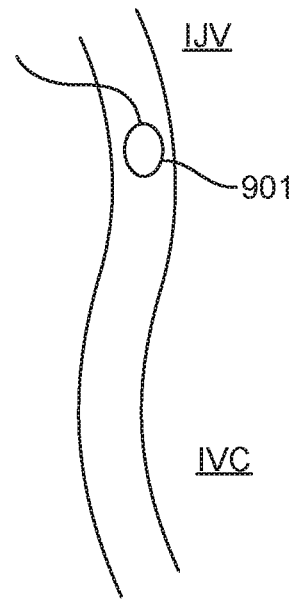
FIG. 9 illustrates an exemplary embodiment of a snare introduced into an internal jugular vein.

FIGS. 3 and 4 illustrate exemplary embodiments of a cross-section of a catheter from a hemodynamic support device or system, either of which may be used in the exemplary delivery methods previously described in FIGS. 2A-2F. FIG. 3 shows the cross-section of a catheter with two lumens each having a circular cross-section, one for inflow 301 and the other for outflow 305 of blood. FIG. 4 depicts the cross-section of a catheter with two D-shaped lumens, one for inflow 401 and the other for outflow 405 of blood. One of skill in the art will appreciate that other lumen cross-sectional geometries may be used, and the lumen configurations are not limited to circular or D-shaped. Optionally, in other embodiments, the diameter or the shapes of the two lumens can be the same. One of skill in the art will also appreciate that the lumen may be made of different materials. The aforementioned features directed to the catheter are not mandatory and may be used in any embodiment. These catheters may be used with any of the other methods or systems described therein and further may be used in combination with or substituted with any catheter, catheter system, hemodynamic support device, guide wire, snare, hemodynamic support system, or any other method of providing hemodynamic support to a patient described herein FIG. 5 illustrates an exemplary embodiment of a hemodynamic support system 501 with a pump 505 and a catheter 510 to be inserted through the vein as previously described in FIGS. 2A-2F. Non-limiting examples of hemodynamic support systems with pumps include: the TandemHeart™ Percutaneous Ventricular Assist Device (pVAD), the Impella, the CentriMag left ventricular assist system, percutaneous heart pumps, and extracorporeal membrane oxygenation (ECMO) devices. Optionally, in other embodiments, the pump is coaxial, centrifugal, or any other pump that aspirates the blood from one chamber of the heart via an inlet catheter and delivers the blood to the aorta or the left ventricular outflow tract via an outlet catheter. The blood may optionally be delivered from the patient to the hemodynamic support system 501 through one lumen in the catheter 510 and then delivered to the pump 505 which then pumps the blood back to the body through another lumen in the same catheter 510. By letting the hemodynamic support system remove the blood and pump it back into the body, this alleviates the work on the heart. Alleviating the work on the heart allows the heart to rest and recover as a bridge to awaiting a heart transplant or other therapies, or in certain circumstances allow the heart to heal on its own. These hemodynamic support systems may be used with any of the other methods or systems described therein and further may be used in combination with or substituted with any catheter, catheter system, hemodynamic support device, guide wire, snare, hemodynamic support system, or any other method of providing hemodynamic support to a patient described herein FIGS. 6A-6D illustrate exemplary embodiments of a catheter with three ports, two ports on the proximal portion of the catheter 660 and a third port with varying configurations on the distal portion of the catheter 650. One of skill in the art will appreciate that the catheter can have many shapes based on the configuration of the two ports on the proximal portion 660, including, but not limited to a Y-shape or a T-shape. FIG. 6A illustrates an exemplary embodiment of a catheter with a cage configuration in the distal portion 650. FIG. 6A further illustrates an exemplary embodiment of a plurality of optional apertures 601 circumferentially disposed around the distal portion of the catheter 650. FIG. 6A also displays an exemplary embodiment of the plurality of axially oriented elongate elements 605 where the elements 605 expand radially and outwardly from the distal end of the catheter 650, curve towards the proximal portion of the catheter 660, and connect with the catheter at a location proximal to the distal end. In some embodiments the radially expanding elements 605 are self-expanding to form a basket or cage at the distal portion of the catheter 650. The basket or cage prevents surrounding heart tissue from interfering with blood as the blood is drawn into the distal portion of the catheter 650. FIG. 6B illustrates an exemplary embodiment of a catheter with a distal portion of the catheter 650 flared to form a trumpet shape 610. FIG. 6C illustrates an exemplary embodiment of a catheter with a combination of a cage and trumpet configuration 615 at the distal portion 650 where it has a plurality of wires or filaments that extend across the flared portion of the catheter and form a barrier that prevents surrounding heart tissue from interfering with blood as the blood is drawn into the distal portion of the catheter 650. FIG. 6D illustrates an exemplary embodiment of a catheter with a cage configuration with a plurality of radially expandable elements 625 extending radially outward and past the distal end of the catheter 650, curve towards the proximal portion of the catheter 660, and connects with the catheter at a location proximal to the distal end. Optionally, in this or other embodiments, the radially expandable elements may be made of NITINOL material to collapse during delivery and expand in the body to anchor the tip of the catheter in the intended cardiac chamber and prevent the catheter from migrating. FIG. 6D further displays an exemplary embodiment of the plurality of optional apertures 620 circumferentially disposed around the distal portion of the catheter. The radially expanding elements 625 may optionally be self-expanding to form a basket or cage at the distal portion of the catheter 650. The basket or cage prevents surrounding heart tissue from interfering with blood as the blood is drawn into the distal portion of the catheter 650. Use of the embodiments described in FIGS. 6A-6D is described elsewhere in this specification. This catheter may be used with any of the other methods or systems described therein and further may be used in combination with or substituted with any catheter, catheter system, hemodynamic support device, guide wire, snare, hemodynamic support system, or any other method of providing hemodynamic support to a patient described herein FIG. 7 illustrates an exemplary embodiment of an inner catheter 705 disposed in one of three ports of an outer catheter 710. FIG. 7 displays an exemplary embodiment of the inner catheter 705 being introduced through a port 715 located in a proximal portion of the outer catheter 710. FIG. 7 further demonstrates an exemplary embodiment of the inner catheter 705 exiting a third port 720 located at a distal portion of the outer catheter 710. The third port 720 may optionally be configured to act as an inlet so that blood may be delivered from the heart or adjacent vasculature to another portion of a hemodynamic support system. Optionally, the distal portion of the inner catheter 725 may be an outlet port configured to deliver blood from another portion of the hemodynamic support system back to the heart. The outer catheter 710 may optionally have a plurality of optional apertures circumferentially disposed around the distal portion of the outer catheter that also act as inlet ports to deliver blood from the heart to another portion of the hemodynamic support system. The distal portion of the outer catheter may optionally have protruding elements or flares of varying degrees designed to form a barrier around the third port or plurality of apertures to prevent heart tissue from interfering with the delivery of blood, such as the optional features described in FIGS. 6A-6D. These inner and outer catheters may be used with any of the other methods or systems described therein and further may be used in combination with or substituted with any catheter, catheter system, hemodynamic support device, guide wire, snare, hemodynamic support system, or any other method of providing hemodynamic support to a patient described herein FIGS. 8A-8E illustrates an exemplary embodiment of delivery of the inner and outer catheters 705 and 710 from FIG. 7, advancing in the heart in an antegrade fashion where the distal end of the outer catheter is disposed in the vena cava VC or any position proximal of the catheter inlet ports, and the distal portion of the inner catheter is disposed in the aorta AO. FIG. 8A illustrates the outer catheter 710 disposed in the vena cava VC. FIG. 8B illustrates an exemplary embodiment of the inner catheter 705 advancing through the outer catheter 701 and into the right atrium RA in an antegrade fashion. FIG. 8C illustrates the inner catheter 705 advancing transseptally from the right atrium RA into the left atrium LA in an antegrade fashion. FIG. 8D illustrates the inner catheter 705 advancing from the right atrium RA across the mitral valve MV in an antegrade fashion. FIG. 8E illustrates the inner catheter 705 advancing toward the left ventricular outflow tract 215 until the distal portion of the inner catheter 725 is disposed in the aorta AO. Optionally, the distal portion of the outer catheter 720 may be located at a location proximal of the distal portion of the inner catheter 725. Non-limiting examples of where the distal portion of the outer catheter 720 can be located include: the vena cava VC, the right atrium RA, the left atrium LA, or the left ventricle LV. Optionally, in other embodiments, the outer catheter may be aspirating blood from the vena cava VC, right atrium RA, left atrium LA, or left ventricle LV. In instances where the distal portion of the outer catheter 720 is disposed in areas of the heart where the surrounding blood is not yet oxygenated from the lungs, e.g., vena cava VC or right atrium RA, the blood may be delivered to another portion of the hemodynamic support system that oxygenates the delivered blood and remove the CO2 such as with an extra corporeal membrane oxygenation (ECMO) system. In instances where the distal portion of the outer catheter 720 is disposed in areas of the heart where the surrounding blood has already been oxygenated from the lungs, e.g., left atrium LA or left ventricle LV, the blood may be delivered to another portion of the hemodynamic support system without requiring the oxygenation by a machine. Optionally the outer catheter 710 has a plurality of apertures circumferentially disposed around the distal portion of the catheter to act as inlet ports to deliver blood from the heart to another portion of the hemodynamic support system. The distal portion of the outer catheter 710 may optionally have protruding elements or flares of varying degrees designed to form a barrier around the third port or plurality of apertures to prevent heart tissue from interfering with the delivery of blood, such as those previously described in FIGS. 6A-6D. This method of delivering the inner and outer catheter may be used with any of the other methods or systems described therein and further may be used in combination with or substituted with any catheter, catheter system, hemodynamic support device, guide wire, snare, hemodynamic support system, or any other method of providing hemodynamic support to a patient described herein FIG. 9 illustrates an exemplary embodiment of a snare 901 introduced into an internal jugular vein IJV, the subclavian vein or any other vein that empties into the subclavian vena cava (SVC).

Figure 10:
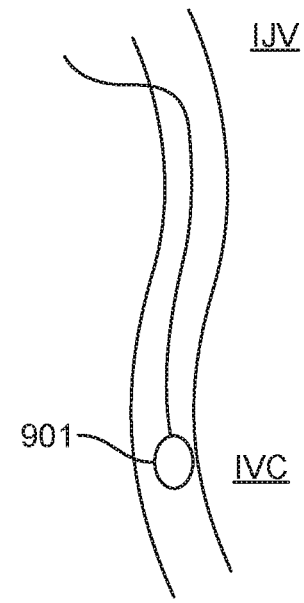
FIG. 10 illustrates an exemplary embodiment of the snare in FIG. 9 advancing to an inferior vena cava.

FIG. 10 illustrates the snare 901 advancing to an inferior vena cava IVC.

Figure 11:
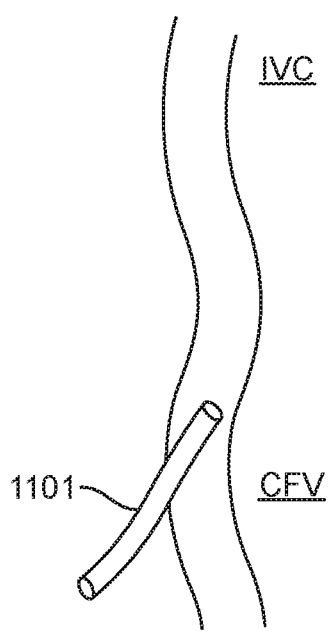
FIG. 11 illustrates an exemplary embodiment of a catheter introduced into a common femoral vein.

FIG. 11 illustrates an exemplary embodiment of a catheter 1101 introduced into a common femoral vein CFV.

Figure 12:
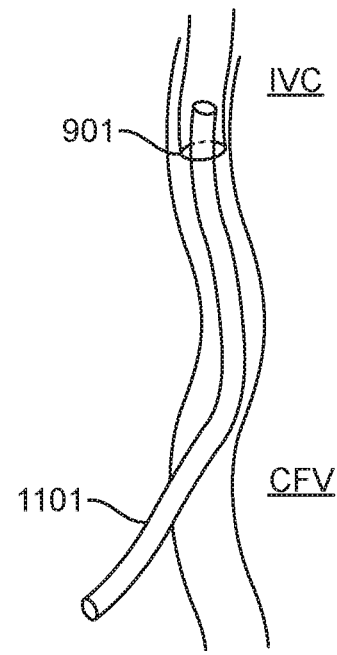
FIG. 12 illustrates an exemplary embodiment of the catheter in FIG. 11 advancing through the snare in FIG. 9.

FIG. 12 illustrates the catheter 1101 advancing through the snare 901 into an inferior vena cava IVC.

Figure 13:
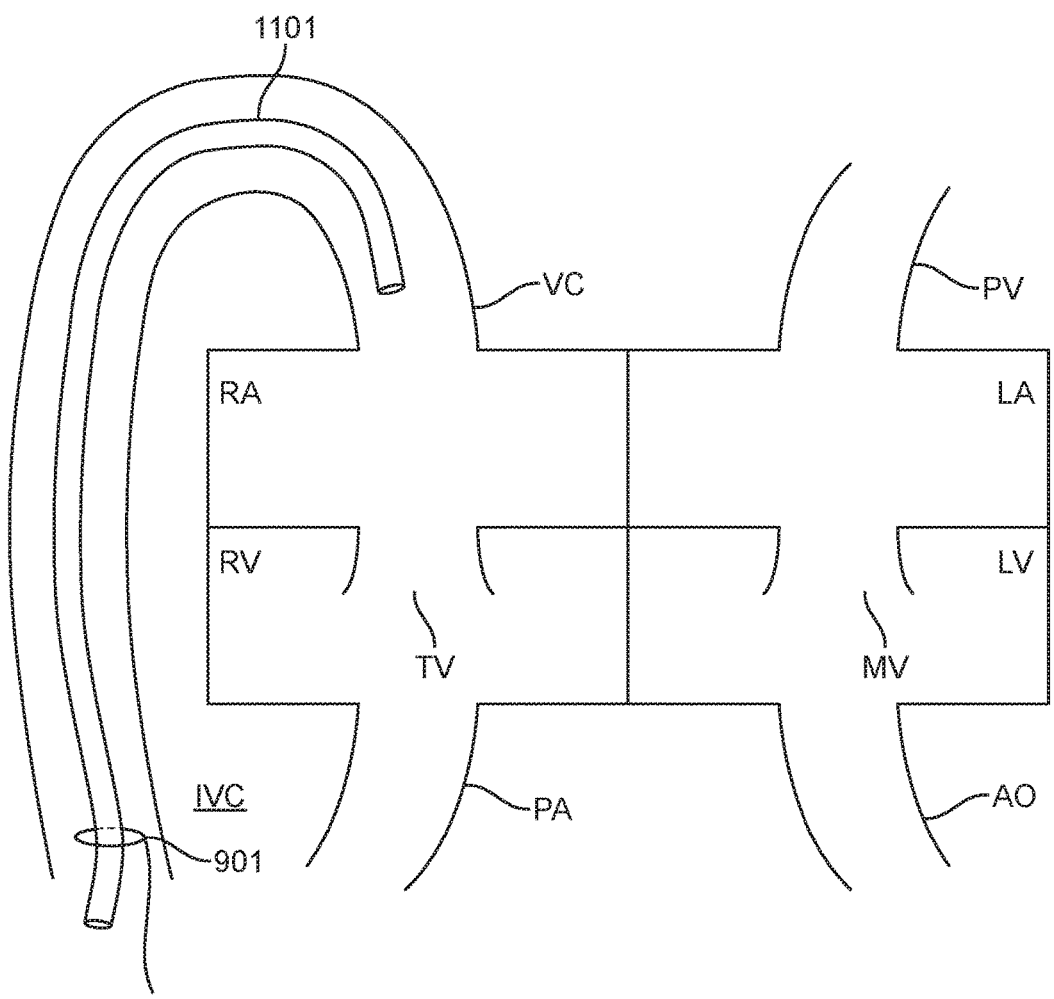
FIGS. 13-16 illustrate an exemplary embodiment of the catheter in FIG. 11 advancing through the snare in FIG. 9, through the vena cava, through the right atrium, transseptally into the left atrium, across the mitral valve, through the left ventricle, and into the aorta in an antegrade fashion.

FIG. 13 illustrates the catheter 1101 advancing through the snare 901 into the vena cava VC in an antegrade fashion.

Figure 14:
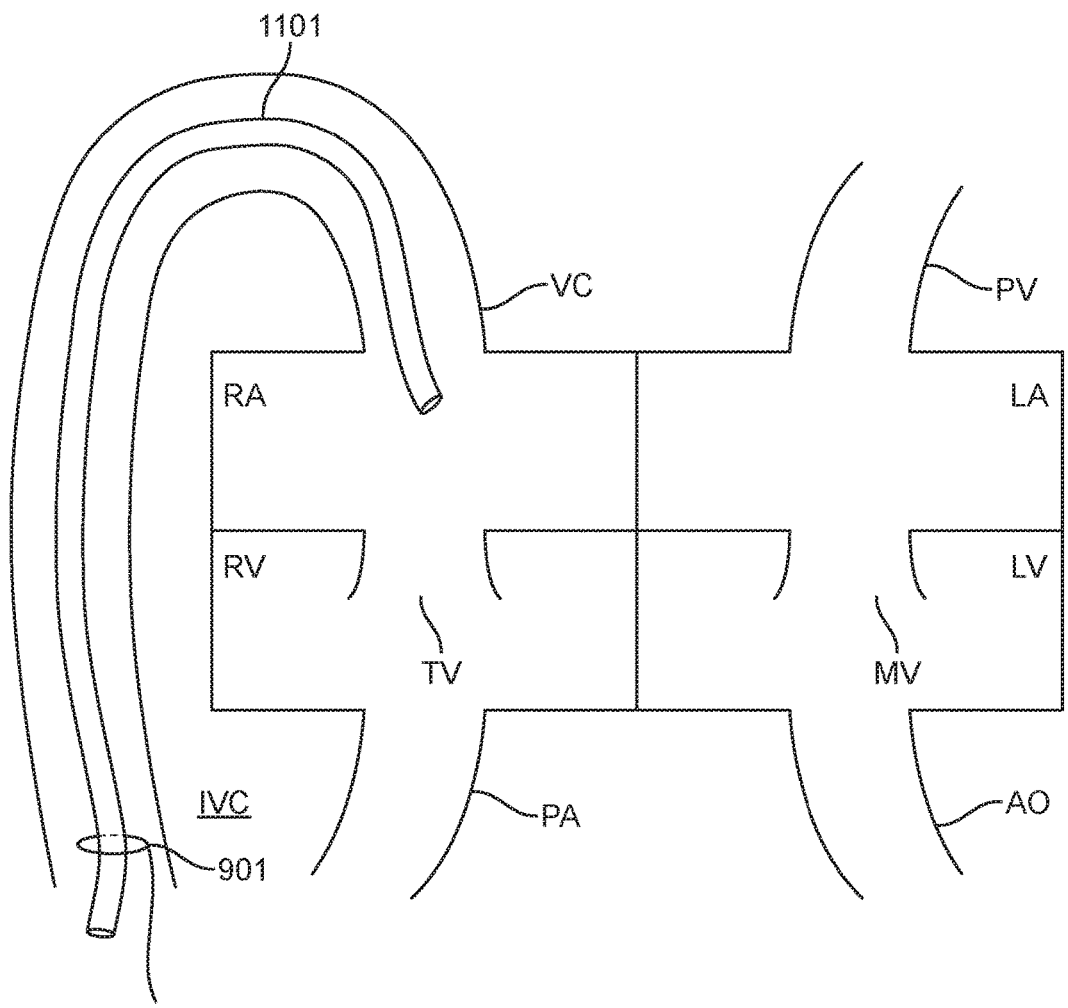

FIG. 14 illustrates the catheter 1101 advancing through the snare 901 into the right atrium RA in an antegrade fashion.

Figure 15:
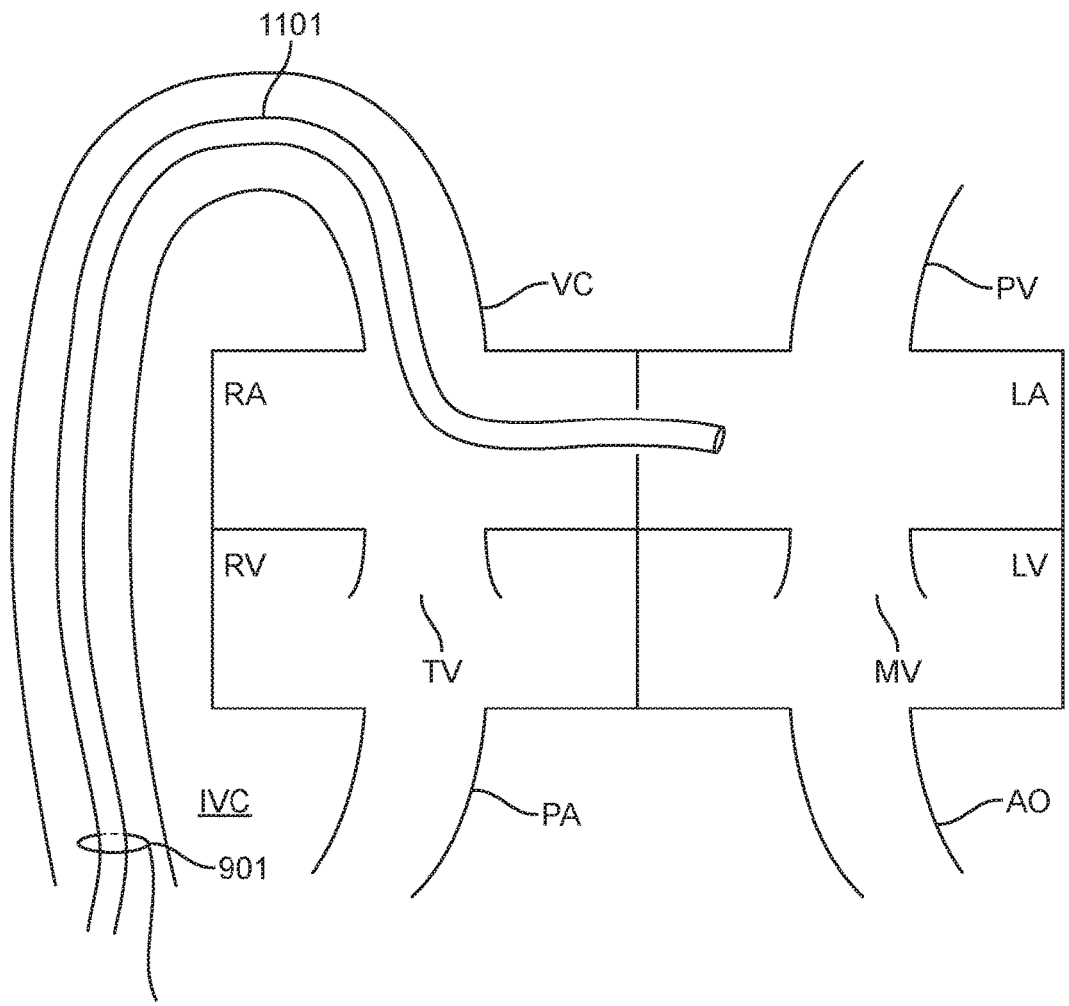

FIG. 15 illustrates the catheter 1101 advancing through the snare 901 and advancing transseptally from the right atrium RA into the left atrium LA in an antegrade fashion.

Figure 16:
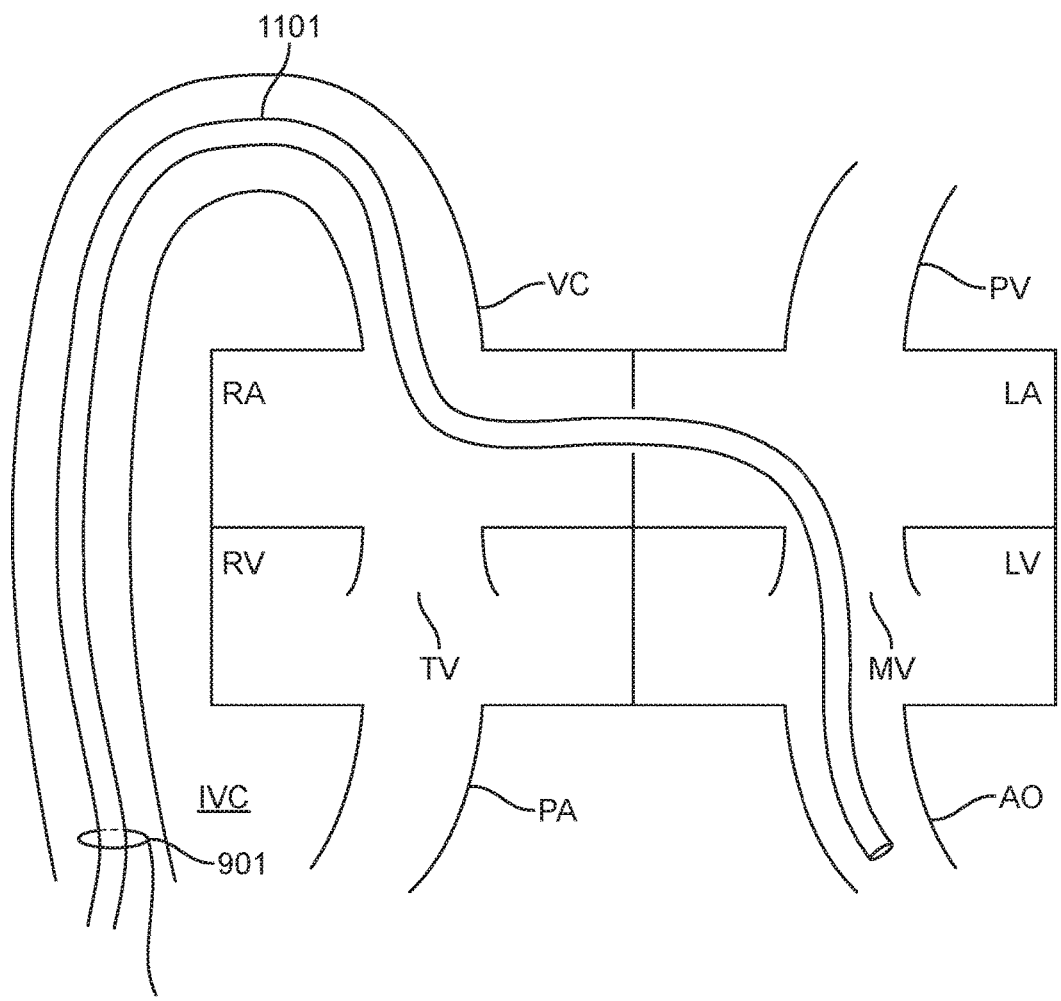

FIG. 16 illustrates the catheter 1101 advancing through the snare 901 and advancing across the mitral valve MV and left ventricular outflow tract 215 into the aorta AO in an antegrade fashion. This method of introducing a snare and advancing the catheter described in FIGS. 9-16 may be used with any of the other methods or systems described therein and further may be used in combination with or substituted with any catheter, catheter system, hemodynamic support device, guide wire, snare, hemodynamic support system, or any other method of providing hemodynamic support to a patient described herein.

Figure 17:
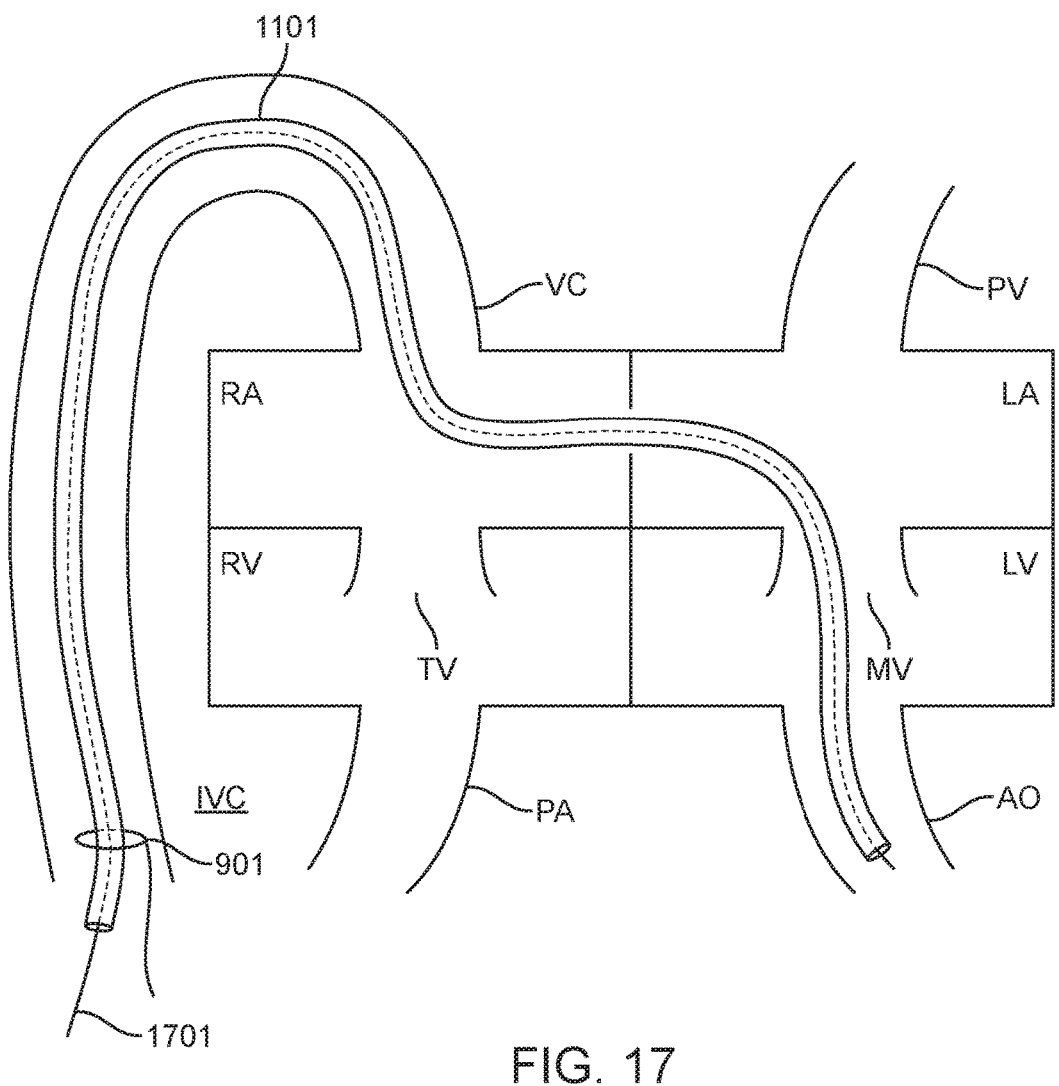
FIG. 17 illustrates an exemplary embodiment of a guide wire advanced over the catheter in FIG. 11 and the snare in FIG. 9 in an antegrade fashion.

FIG. 17 illustrates an exemplary embodiment of a guide wire 1701 advancing through the catheter 1101 and through the snare 901 in antegrade fashion to the ascending aorta AO.

Figure 18:
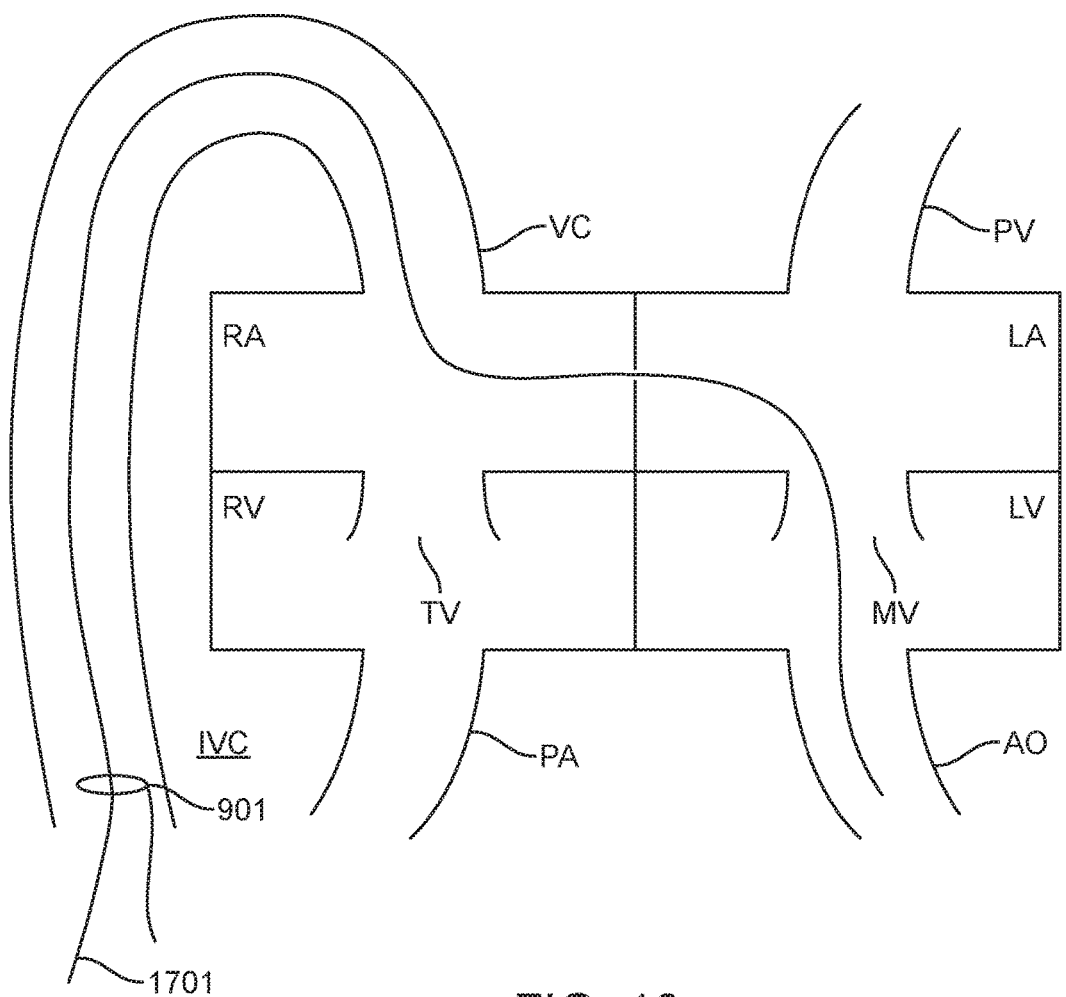
FIG. 18 illustrates an exemplary embodiment of the guide wire in FIG. 17 remaining after the catheter in FIG. 12 is removed.

FIG. 18 illustrates the guide wire 1701 remaining in the heart and through the snare 901 after the catheter 1101 is removed.

FIG. 19 illustrates the snare 901 externalizing a proximal portion of the guide wire 1701 from the internal jugular vein IJV, the subclavian vein, or any other vein that empties into the SVC. In some embodiments the snare may externalize a different portion of the guide wire 1701. This method of externalizing the guide wire may be used with any of the other methods or systems described therein and further may be used in combination with or substituted with any catheter, catheter system, hemodynamic support device, guide wire, snare, hemodynamic support system, or any other method of providing hemodynamic support to a patient described herein.

FIG. 20 illustrates an exemplary embodiment of a catheter 2001 advancing through the guide wire 1701 from the internal jugular vein IJV. The catheter may be any of the catheters described in this specification or known in the art.

FIG. 21 illustrates an exemplary embodiment of the outer catheter 710 advancing over the guide wire 1701 from the internal jugular vein IJV. An inner catheter may optionally be advanced through a port proximal of the distal end of the outer catheter 710. The inner and outer catheters may be positioned as described previously with respect to FIGS. 8A-8E, or if a single multi-lumen catheter is used, it may be positioned as described with respect to FIGS. 2A-2F.

Figure 22:
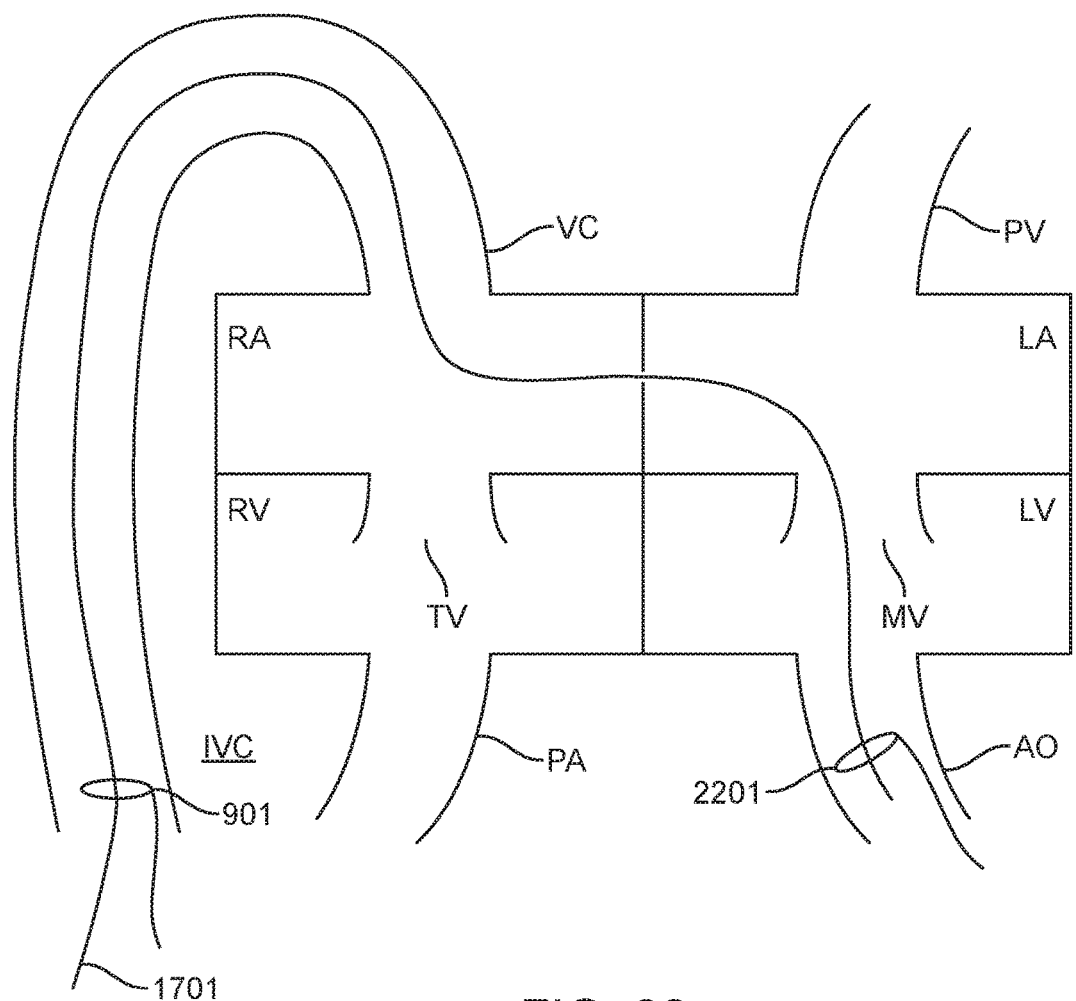
FIG. 22 illustrates an exemplary embodiment of a second snare at a distal portion of the arterial system snaring a distal portion of the guide wire in FIG. 17.

FIG. 22 illustrates an exemplary embodiment of a second snare 2201 in the ascending aorta AO snaring a distal portion of the guide wire 1701. The second snare 2201 may optionally be introduced through an artery, which may include, but is not limited to, a radial artery, a brachial artery, an axillary artery, a subclavian artery, a carotid artery, or common femoral artery, and advanced retrograde into the aorta AO, the LV, or the LA. Optionally, the second snare 2201 may externalize a distal portion of the guide wire 1701 through the vein.

Figure 23:
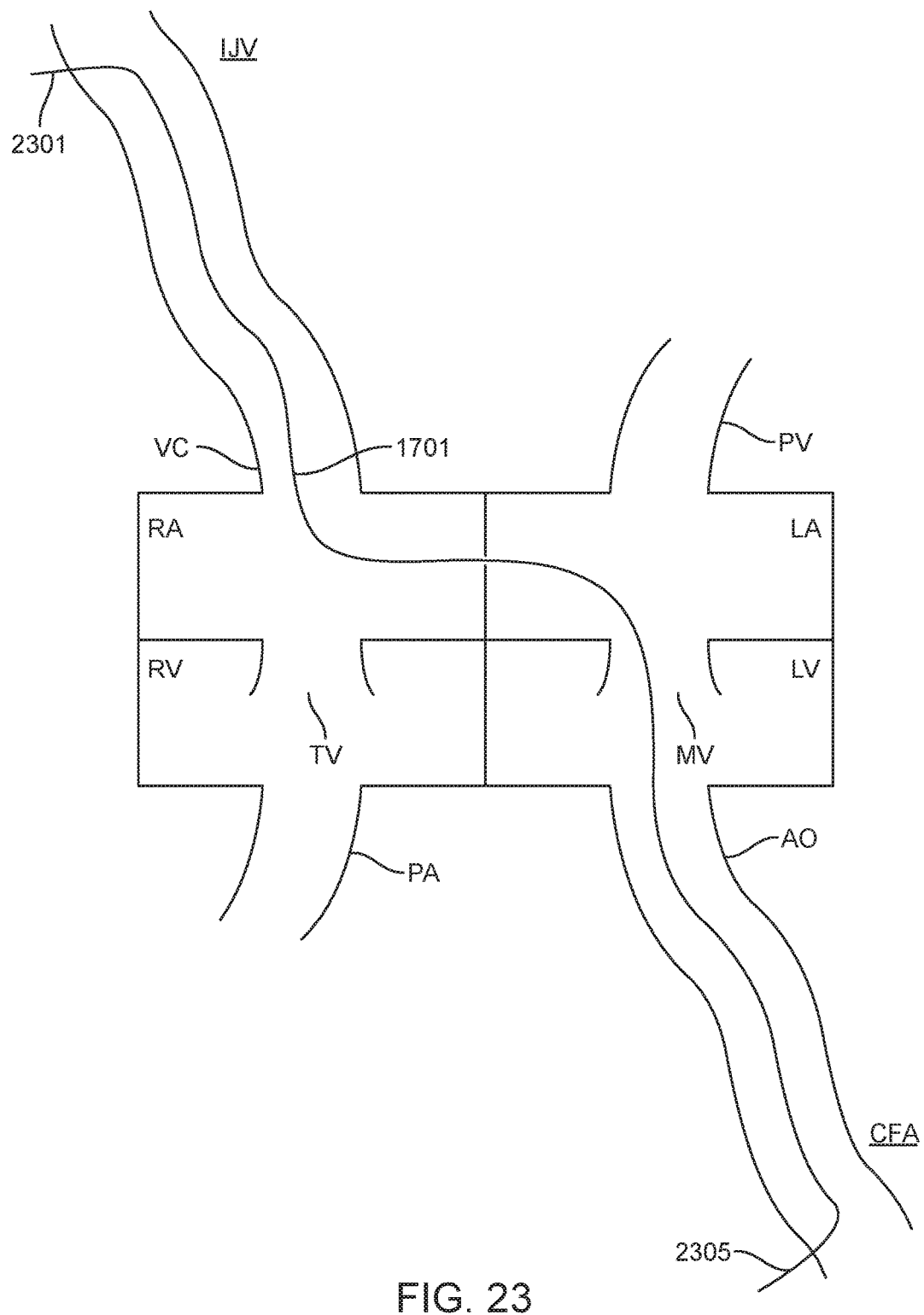
FIG. 23 illustrates an exemplary embodiment of a guide wire advanced through the heart with the one end of the guide wire externalized from the internal jugular vein and the other end of the guide wire externalized from the common femoral artery.

FIG. 23 illustrates an exemplary embodiment of a guide wire 1701 advanced through the vena cava VC, right atrium RA, left atrium LA, left ventricle LV, and aorta AO with one end of the guide wire 2301 externalized from the internal jugular vein IJV and the other end of the guide wire 2305 externalized from a common femoral artery CFA. One end of the guide wire 2305 may optionally be externalized from any artery, including, but not limited to, a common femoral artery, radial artery, brachial artery, or an axillary artery. This method of externalizing the guide wire may be used with any of the other methods or systems described therein and further may be used in combination with or substituted with any catheter, catheter system, hemodynamic support device, guide wire, snare, hemodynamic support system, or any other method of providing hemodynamic support to a patient described herein.

Figure 24:
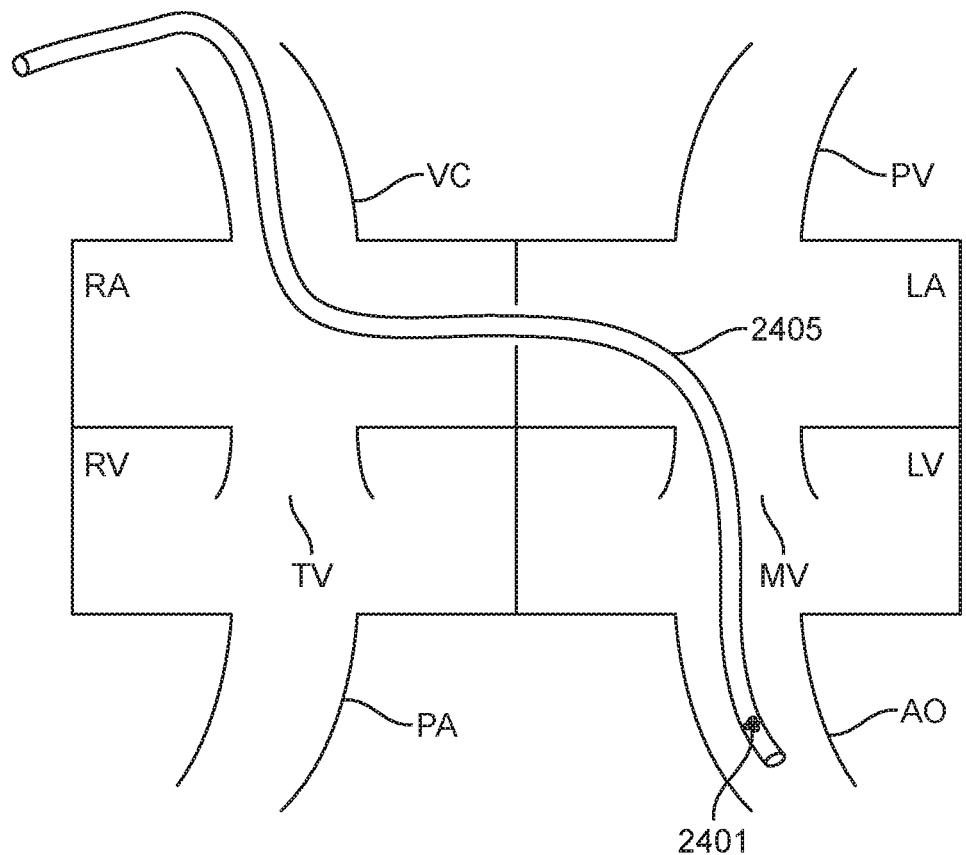
FIG. 24 illustrates an exemplary embodiment of a hemodynamic support device with a pump disposed in an aorta and an inlet port disposed in a left atrium.

FIG. 24 illustrates an exemplary embodiment of a hemodynamic support device with a pump 2401 disposed in an aorta and an inlet port 2405 disposed in a left atrium. The inlet port may optionally be disposed in a left ventricle. Operating the hemodynamic support device may optionally include introducing blood disposed in the left atrium or the left ventricle into the inlet port of the hemodynamic support device. Optionally, the hemodynamic support device may apply a treatment to blood in the aorta. Optionally, applying a treatment to blood in the aorta may comprise pumping blood disposed in the left atrium or the left ventricle or both the left atrium and left ventricle directly into the aorta. All or a portion of the hemodynamic support device with a pump 2401 may optionally be in the aorta. Optionally, the hemodynamic support device may operate where the blood is not pumped outside the body. The hemodynamic support device may optionally be delivered by any method or by using any catheter, catheter systems, guide wire, hemodynamic support system, or any combination thereof described in the specification herein.

Figure 25:
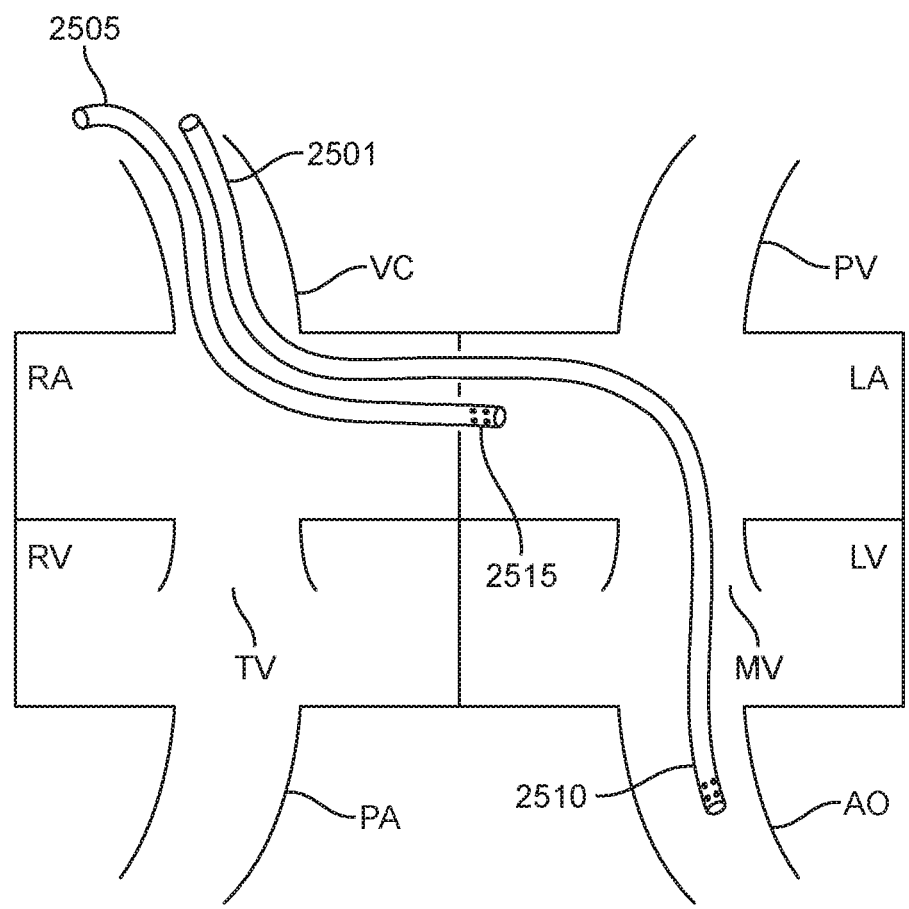
FIGS. 25-27 illustrate exemplary embodiments of a hemodynamic support system with two separate catheters.
Figure 26:
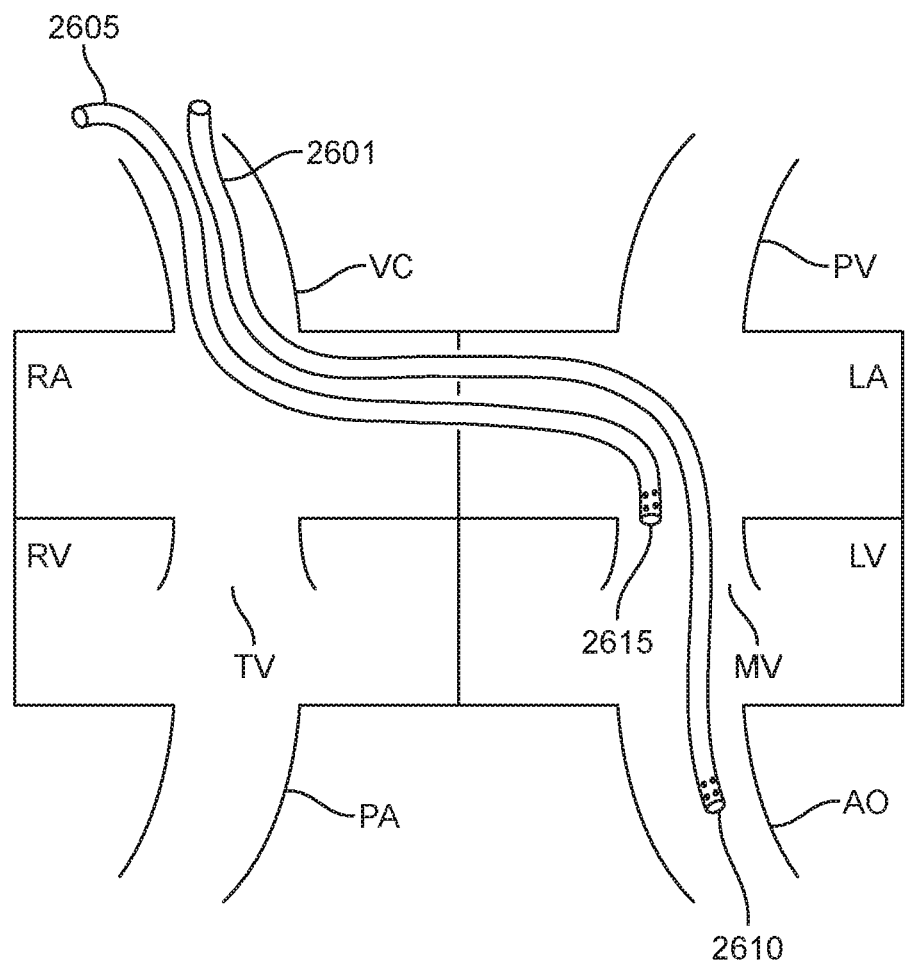
Figure 27:
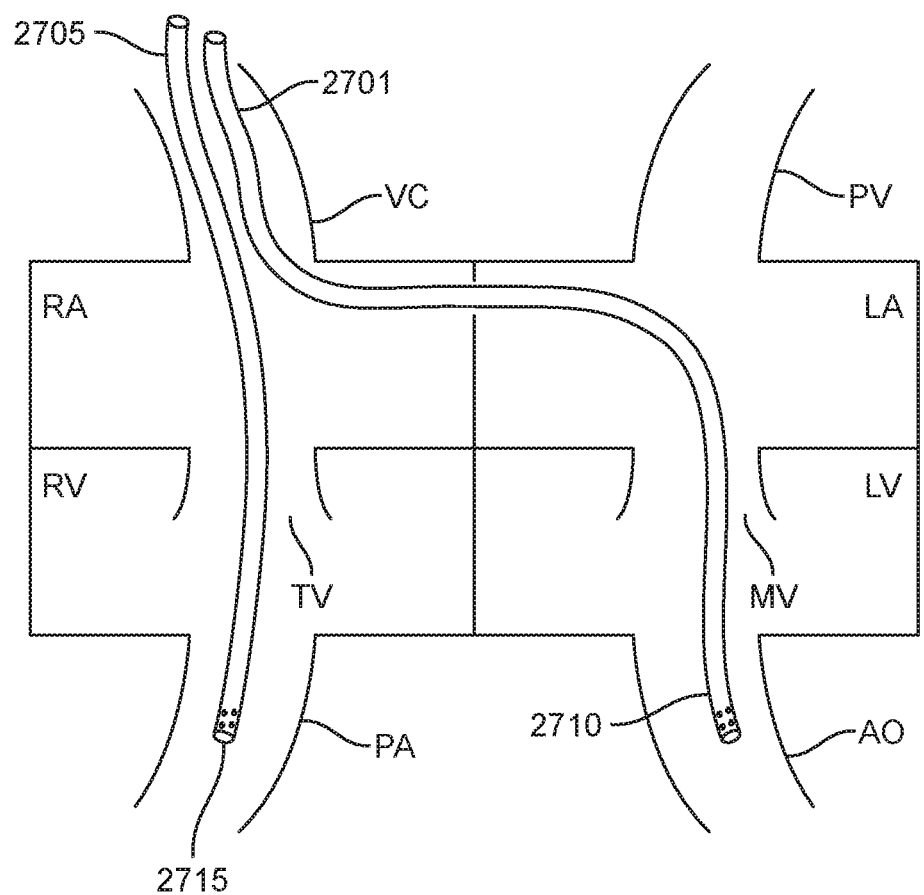

FIGS. 25-27 illustrate exemplary embodiments of a hemodynamic support system with two separate catheters. FIG. 25 portrays an inlet catheter 2505 and an outlet catheter 2501, the inlet catheter 2505 comprising an inlet port 2515 disposed on a distal portion thereof and an outlet catheter comprising an outlet port 2510 disposed on a distal portion thereof, in a patient's heart. Optionally, in other embodiments, the outlet catheter comprises an additional lumen. Optionally, in other embodiments, additional outlet ports are disposed on the outlet port to deliver blood to the left ventricle, left atrium, or both. The outlet catheter 2501 is optionally introduced into a vein of the patient using any of the methods described herein or known in the art. The outlet catheter 2501 is also optionally advanced in an antegrade direction into an aorta AO, wherein the outlet port 2510 is disposed in the aorta AO. The inlet catheter 2505 may also be optionally introduced into a vein of the patient using any of the methods described herein or known in the art. The inlet catheter 2505 may optionally be advanced proximal to the outlet port 2510. In the present embodiment, the outlet port 2510 is disposed in the aorta while the inlet port 2515 is disposed in the left atrium. However, the inlet port may optionally be disposed anywhere proximal to the outlet port 2510. Examples of where the inlet catheter may be disposed include, but are not limited to, the left ventricle, the left atria, mitral valve, anywhere in the right heart (including the right atrium, right ventricle, tricuspid valve), the pulmonary artery, or anywhere in the venous system. Optionally, the patient's blood may be removed through the inlet catheter 2505 via the inlet port 2515 and delivered to another portion of the hemodynamic support system. Optionally, the patient's blood may be returned to the patient by delivering the blood to the aorta AO through the outlet catheter 2501 via the outlet port 2510. Optionally, this method may alleviate the workload on the patient's heart and support the normal body functions.

Optionally, introducing either the inlet or outlet catheter a vein of the patient may comprise introducing a guide wire into the vein and advancing either the inlet or outlet catheter over the guide wire. Optionally, introducing either the inlet or outlet catheters into a vein of the patient may comprise accessing the common femoral vein with either catheter or introducing either catheter into an internal jugular vein, thereby permitting increased patient mobility. Optionally, advancing the outlet catheter in an antegrade direction into an aorta may comprise advancing the outlet catheter into an ascending aorta. Optionally, advancing the outlet catheter in an antegrade direction into an aorta may also comprise advancing the outlet catheter in an antegrade direction into a vena cava, advancing the outlet catheter in the antegrade direction into a right atrium, passing the outlet catheter transseptally form the right atrium into a left atrium, advancing the outlet catheter across a mitral valve, and advancing the outlet catheter in the antegrade direction through a left ventricular outflow tract into the aorta. Optionally, the inlet port may be disposed in the left atrium, left ventricle, anywhere in the venous system, anywhere in the right heart (including, but not limited to, the right atrium, tricuspid valve, and right ventricle) or the pulmonary artery. Optionally, the inlet catheter may have a plurality of apertures dispose on the catheter to act as anchor of the catheter and prevent inlet port obstruction by the surrounding tissues. The plurality of apertures may further be circumferentially disposed around the distal portion of the inlet catheter or disposed throughout the entire inlet catheter. By way of example, the plurality of apertures may be disposed axially along the catheter, helically around the catheter, or randomly along the catheter. The inlet catheter may optionally also comprise a plurality of axially oriented elongate elements disposed along the distal portion of the inlet catheter, whereby the plurality of elongate elements radially expand to form a barrier around the inlet port or the plurality of apertures wherein the barrier prevents tissue from obstructing the inlet port or the plurality of apertures. The distal portion of the inlet catheter may optionally be flared to form a trumpet shape. Optionally, the plurality of radially expandable elements may be self-expanding. Optionally, the plurality of radially expandable elements extend radially outward from the distal end of the inlet catheter, curve towards the proximal portion of the inlet catheter, and connect with the inlet catheter at a location proximal to the distal end. Optionally, the plurality of radially expandable elements extend radially outward and past the distal end of the inlet catheter, curve towards the proximal portion of the inlet catheter, and connect with the inlet catheter at a location proximal to the distal end. Optionally, removing blood from the patient through the inlet catheter may comprise removing unoxygenated blood from the right side of the heart or a vessel coupled to the right side of the heart. Optionally, the inlet and outlet catheters are introduced in to the same vein or different vein. The method may also optionally be performed without large bore arterial access or be provided to a patient having peripheral artery disease. The method may optionally comprise delivering the blood to a portion of the hemodynamic support system that is a pump. If the delivered blood is deoxygenated, the pump comprises an extra corporeal membrane oxygenator system. Optionally, in this or other embodiments, the pump is integrated inside the catheter, similar to Impella® or the HeartMate™ PHP Catheter Pump. Optionally, in this or other embodiments, the pump is separate and sits outside the body. Optionally, in this or other embodiments, the pump is implanted under the skin. These methods may also be optionally used in combination with or substituted with any catheter, catheter system, hemodynamic support device, guide wire, snare, hemodynamic support system, or any other method of providing hemodynamic support to a patient described herein. This includes, by way of example, the plurality of axially oriented elongate elements or the trumpet shape being disposed in the distal portion of the inlet or outlet catheter.

FIG. 26 illustrates an exemplary embodiment of a hemodynamic support system with two separate catheters, an inlet catheter 2605 and an outlet catheter 2601, the inlet catheter 2605 comprising an inlet port 2615 disposed on a distal portion thereof and an outlet catheter comprising an outlet port 2610 disposed on a distal portion thereof, in a patient's heart. In the present embodiment, the outlet port 2510 is disposed in the aorta while the inlet port 2515 is disposed in the left ventricle. However, as described above, the inlet port may optionally be disposed anywhere proximal to the outlet port 2610. The catheters may be delivered using any of the methods described herein or known in the art. Examples of where the inlet catheter may be disposed include, but are not limited to, the left ventricle, left atria, mitral valve, anywhere in the right heart (including the right atrium, right ventricle, tricuspid valve), the pulmonary artery, or anywhere in the venous system. These methods may also be optionally used in combination with or substituted with any catheter, catheter system, hemodynamic support device, guide wire, snare, hemodynamic support system, or any other method of providing hemodynamic support to a patient described herein. The inlet port configuration and outlet port configuration may also take the form of any inlet or outlet port configurations described in the specification, including but not limited to those previously described with respect to FIG. 25. Other features described elsewhere such as the flared trumped or radially expandable cage may be used with this or any other catheter embodiments disclosed herein.

FIG. 27 illustrates an exemplary embodiment of a hemodynamic support system with two separate catheters, an inlet catheter 2705 and an outlet catheter 2701, the inlet catheter 2705 comprising an inlet port 2715 disposed on a distal portion thereof and an outlet catheter comprising an outlet port 2710 disposed on a distal portion thereof, in a patient's heart. These catheters may be delivered using any of the methods described in this specification or known in the art. Also, other features described in other embodiments may optionally be used with these catheters such as the trumped shaped tip or the radially expandable cage, or other features. In the present embodiment, the outlet port 2710 is disposed in the aorta while the inlet port 2715 is disposed in a pulmonary artery. However, as described above, the inlet port may optionally be disposed anywhere proximal to the outlet port 2710. Examples of where the inlet catheter may be disposed include, but are not limited to, the left ventricle, left atrium, mitral valve, anywhere in the right heart (including the right atrium, right ventricle, tricuspid valve), the pulmonary artery, or anywhere in the venous system. Moreover, as described above, the inlet catheter may have a plurality of apertures disposed on the catheter to act as further inlets. Similarly, the outlet catheter may also have any of the other outlet apertures described herein to deliver a fluid to the patient. The plurality of apertures may further be circumferentially disposed around the distal portion of the inlet catheter or disposed throughout the entire venous system or the entire inlet catheter, such as previously described above. These methods may also be optionally used in combination with or substituted with any catheter, catheter system, hemodynamic support device, guide wire, snare, hemodynamic support system, or any other method of providing hemodynamic support to a patient described herein.

Figure 28:
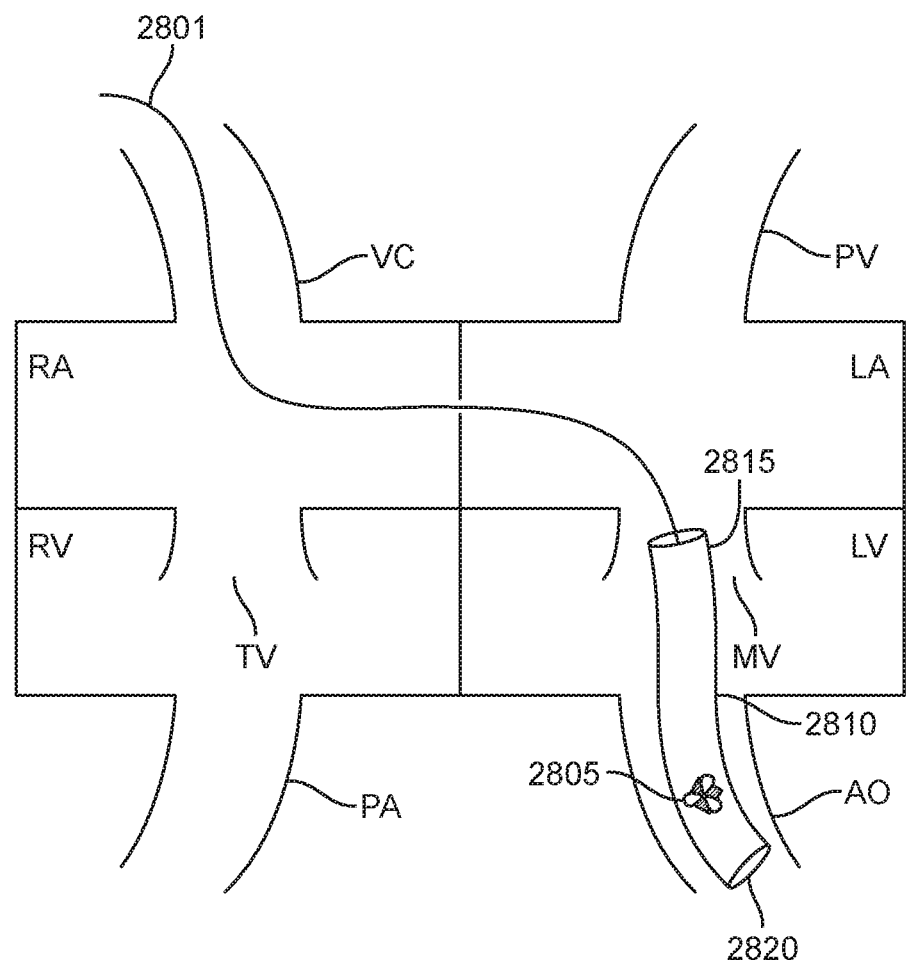
FIGS. 28-30 illustrate exemplary embodiments of a hemodynamic support device and parts therein disposed in different parts of the heart
Figure 29:
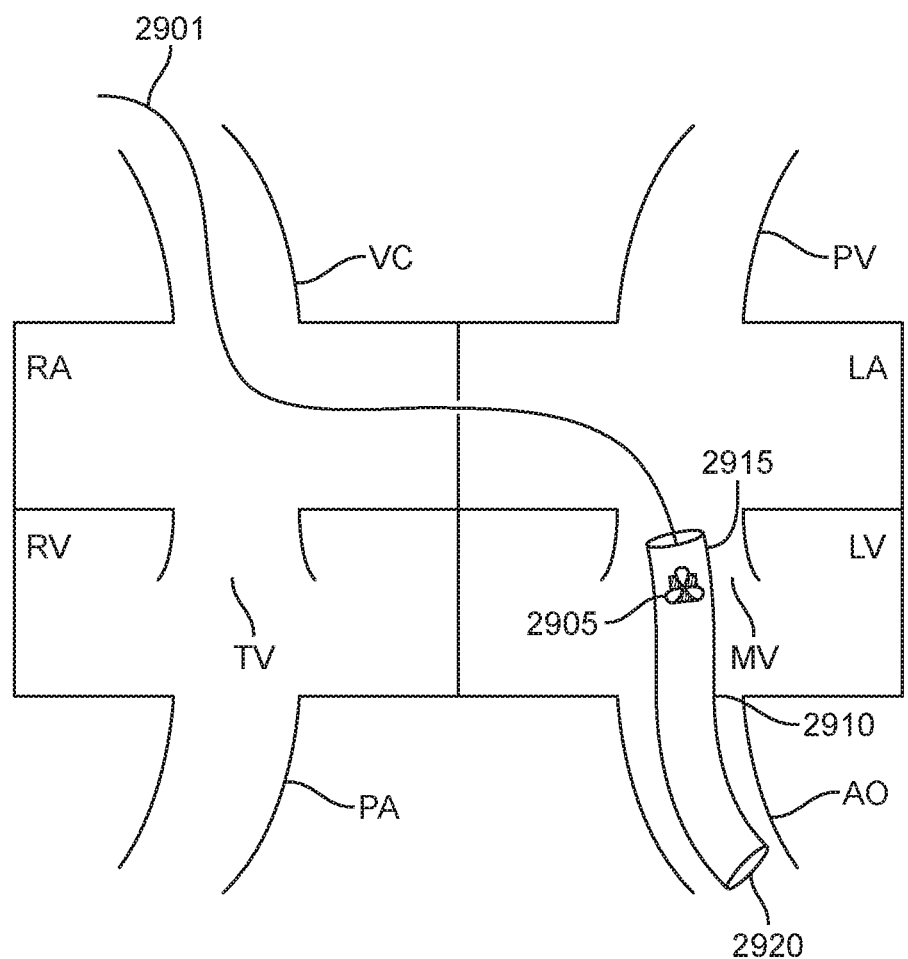
Figure 30:
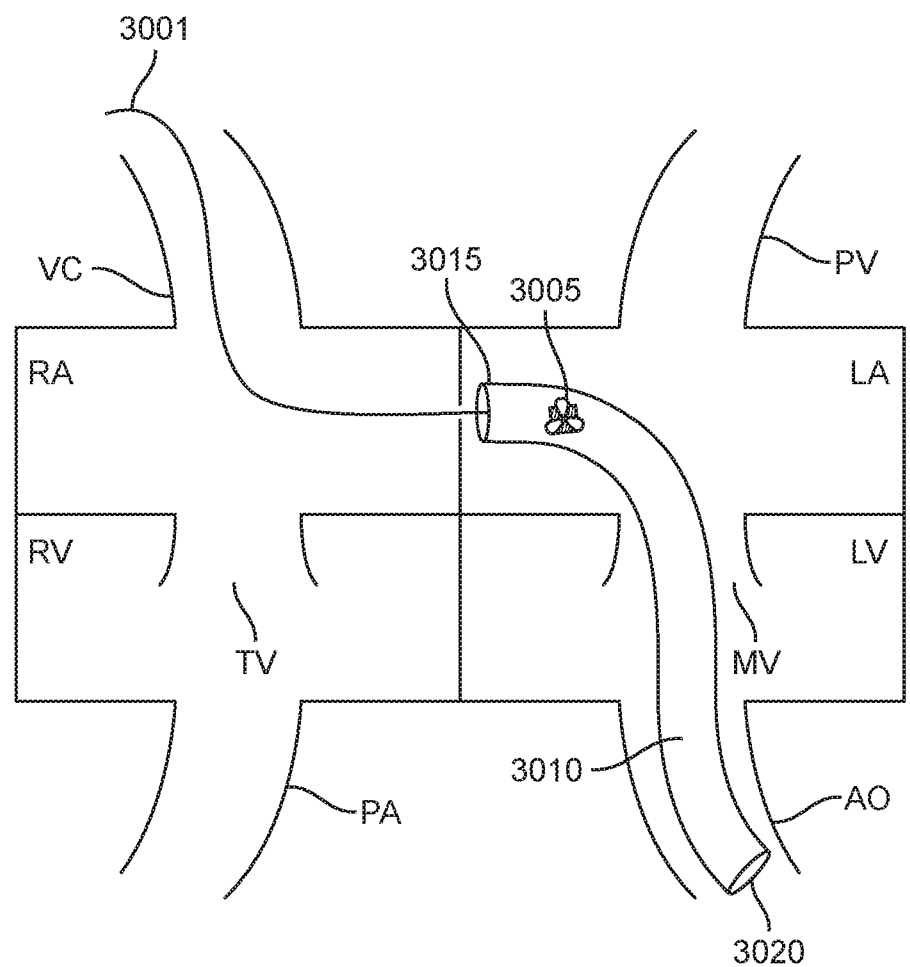

FIGS. 28-30 illustrate exemplary embodiments of a hemodynamic support device and parts therein disposed in different parts of the heart. They may be delivered using any of the methods described in this specification, and may include any of the other features described in other embodiments. FIG. 28 portrays an elongate catheter shaft having a pump 2805 of a hemodynamic support device disposed internally in a catheter 2810. The inlet port 2815 is disposed at a location proximal to the pump 2805. The outlet port 2820 is disposed distal to both the inlet port 2815 and the pump 2805 and may comprise a single distal port at the distal end of the catheter, or may comprise a plurality of outlet ports as previously described in other embodiments herein. Similarly, the catheter may have one inlet port or a plurality of inlet ports such as those previously described. In the present embodiment, the pump 2820 is disposed in the aorta. Optionally, however, the pump may be disposed at any location proximal to the aorta AO, including, but not limited to, the left ventricle LV, the mitral valve MV, or the left atrium LA. Further, the pump may be found at different parts of the catheter, including but not limited to, a proximal portion or the midsection of the catheter as the catheter is disposed in different parts of the heart, including but not limited to, the left atrium, mitral valve, left ventricle, or aorta. In the present embodiment, the proximal end of the catheter 2810 is in the left ventricle LV. Optionally, however, the proximal end may be disposed anywhere in the left heart, including, but not limited to, the left ventricle LV, the mitral valve MV, or the left atrium LA. Optionally, the catheter 2810 may have a plurality of apertures disposed on the catheter 2810 to act as further inlet or outlet ports. The plurality of apertures may further be circumferentially disposed around the proximal portion of the catheter 2810. A plurality of axially oriented elongate elements may also be optionally disposed along the proximal portion of the catheter 2810, whereby the plurality of elongate elements radially expand to form a barrier around the inlet port 2815 or the plurality of apertures wherein the barrier prevents tissue from obstructing the inlet port 2815 or the plurality of apertures. The proximal portion of the catheter 2810 may optionally be flared to form a trumpet shape and may take the form of configurations described in the specification, including but not limited to those previously described with respect to FIGS. 6A-6D. Optionally, the plurality of radially expandable elements may be self-expanding. Optionally, the plurality of radially expandable elements extend radially outward from the proximal end of the catheter 2810, curve towards the distal portion of the catheter 2810, and connect with the catheter 2810 at a location distal to the proximal end. Optionally, the plurality of radially expandable elements extend radially outward and past the proximal end of the catheter 2810, curve towards the distal portion of the catheter 2810, and connect with the catheter 2810 at a location distal to the proximal end. Exiting out of the proximal end of the catheter 2810 is a cord 2801. In some embodiments, the cord 2801 connects the pump 2805 to a power source, which may inside or outside the patient's body, and provides power to the pump, or the cord may be a mechanical connection which transmits torque to the pump to actuate the pump. These methods may also be optionally used in combination with or substituted with any catheter, catheter system, hemodynamic support device, guide wire, snare, hemodynamic support system, or any other method of providing hemodynamic support to a patient described herein. This includes, by way of example, the plurality of axially oriented elongate elements or the trumpet shape being disposed in the distal portion of the catheter.

FIG. 29 illustrates an exemplary embodiment of an elongate catheter shaft having a pump 2905 of a hemodynamic support device disposed internally in a catheter 2910, a cord 2901, an inlet port 2915, and an outlet port 2920. The pump 2905 is disposed internally in a proximal portion of the catheter 2910 and in the left ventricle LV. The pump 2905 may further comprise a single distal port at the distal end of the catheter, or may comprise a plurality of outlet ports as previously described in other embodiments herein. Similarly, the catheter may have one inlet port or a plurality of inlet ports such as those previously described. Optionally, the catheter 2910 may have a plurality of apertures disposed on the catheter 2910 to act as further inlet or outlet ports. The plurality of apertures may further be circumferentially disposed around the proximal portion of the catheter 2910. A plurality of axially oriented elongate elements may also be optionally disposed along the proximal portion of the catheter 2910, whereby the plurality of elongate elements radially expand to form a barrier around the inlet port 2915 or the plurality of apertures wherein the barrier prevents tissue from obstructing the inlet port 2915 or the plurality of apertures. The proximal portion of the catheter 2910 may optionally be flared to form a trumpet shape and may take the form of configurations described in the specification, including but not limited to those previously described with respect to FIGS. 6A-6D. Optionally, the plurality of radially expandable elements may be self-expanding. Optionally, the plurality of radially expandable elements extend radially outward from the proximal end of the catheter 2910, curve towards the distal portion of the catheter 2910, and connect with the catheter 2910 at a location distal to the proximal end. Optionally, the plurality of radially expandable elements extend radially outward and past the proximal end of the catheter 2910, curve towards the distal portion of the catheter 2910, and connect with the catheter 2910 at a location distal to the proximal end. Exiting out of the proximal end of the catheter 2910 is a cord 2901. In some embodiments, the cord 2901 connects the pump 2905 to a power source, which may inside or outside the patient's body, and provides power to the pump, or the cord may be a mechanical connection which transmits torque to the pump to actuate the pump. These methods may also be optionally used in combination with or substituted with any catheter, catheter system, hemodynamic support device, guide wire, snare, hemodynamic support system, or any other method of providing hemodynamic support to a patient described herein.

FIG. 30 illustrates an exemplary embodiment of an elongate catheter shaft having a pump 3005 of a hemodynamic support device disposed internally in a catheter 3010, a cord 3001, an inlet port 3015, and an outlet port 3020. The pump 3005 is disposed internally in a proximal portion of a catheter 3010. The pump 3005 is disposed in the left atrium LA. The pump 3005 is disposed internally in a proximal portion of the catheter 3010 and in the left ventricle LV. The pump 3005 may further comprise a single distal port at the distal end of the catheter, or may comprise a plurality of outlet ports as previously described in other embodiments herein. Similarly, the catheter may have one inlet port or a plurality of inlet ports such as those previously described. Optionally, the catheter 3010 may have a plurality of apertures disposed on the catheter 3010 to act as further inlet or outlet ports. The plurality of apertures may further be circumferentially disposed around the proximal portion of the catheter 3010. A plurality of axially oriented elongate elements may also be optionally disposed along the proximal portion of the catheter 3010, whereby the plurality of elongate elements radially expand to form a barrier around the inlet port 3015 or the plurality of apertures wherein the barrier prevents tissue from obstructing the inlet port 3015 or the plurality of apertures. The proximal portion of the catheter 3010 may optionally be flared to form a trumpet shape and may take the form of configurations described in the specification, including but not limited to those previously described with respect to FIGS. 6A-6D. Optionally, the plurality of radially expandable elements may be self-expanding. Optionally, the plurality of radially expandable elements extend radially outward from the proximal end of the catheter 3010, curve towards the distal portion of the catheter 3010, and connect with the catheter 3010 at a location distal to the proximal end. Optionally, the plurality of radially expandable elements extend radially outward and past the proximal end of the catheter 3010, curve towards the distal portion of the catheter 3010, and connect with the catheter 3010 at a location distal to the proximal end. Exiting out of the proximal end of the catheter 3010 is a cord 3001. In some embodiments, the cord 3001 connects the pump 3005 to a power source, which may inside or outside the patient's body, and provides power to the pump, or the cord may be a mechanical connection which transmits torque to the pump to actuate the pump. These methods may also be optionally used in combination with or substituted with any catheter, catheter system, hemodynamic support device, guide wire, snare, hemodynamic support system, or any other method of providing hemodynamic support to a patient described herein.

Figure 31:
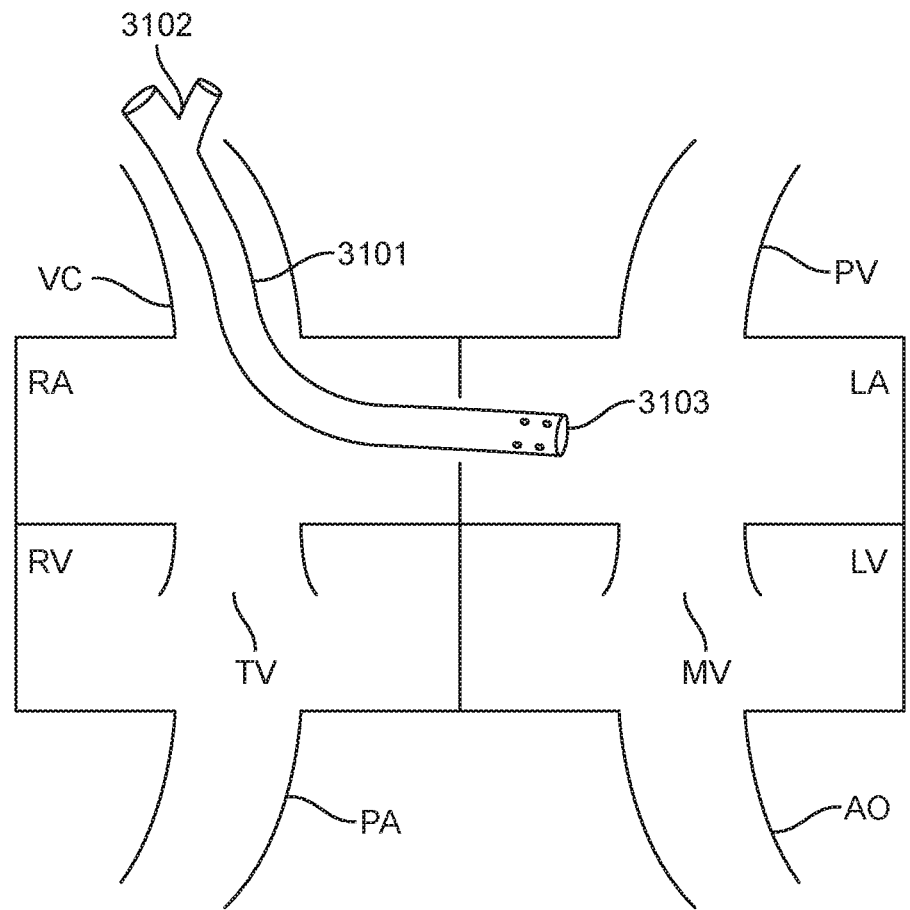
FIG. 31 illustrates an exemplary embodiment of a sheath disposed in the heart.

FIG. 31 illustrates an exemplary embodiment of a sheath 3101 with two proximal heads 3102 and a distal tip 3103, part of a system for providing hemodynamic support to a system, disposed in the left atrium LA. The sheath may be configured for arterial access or more preferably venous access to the heart in an antegrade fashion to introduce any catheter, catheter system, hemodynamic support device, guide wire, snare, hemodynamic support system, or any other method of providing hemodynamic support to a patient described herein. Optionally, the sheath can be configured in shapes that facilitate delivery of any catheter, catheter system, hemodynamic support device, guide wire, snare, hemodynamic support system, or any other method of providing hemodynamic support to any chamber of the heart or the circulatory system. Optionally, the sheath may be peel away sheath so it may be removed by peeling it away leaving behind any of the catheter, catheter system, hemodynamic support device, guide wire, snare, or hemodynamic support system described herein. Optionally, the sheath may have just one proximal head or more than two proximal heads. Optionally, the distal tip of the sheath may be advanced to or disposed in any part of the heart, the venous system, the arterial system, or the circulatory system, including the right atrium RA, right ventricle RV, left ventricle LV, aorta AO, or the left atrium Optionally, the sheath may be configured to remove blood from the heart. Optionally, the sheath can be used in replacement of an inlet or an aspiration catheter, including any of those described herein. Optionally, the sheath may be introduced from the internal jugular vein IJV subclavian vein or from any of the typical groin access points such as the femoral artery or the femoral vein. Optionally, the proximal head may have a valve such as a duckbill valve or Tuohy-Borst valve for sealing off the proximal end to prevent blood or air flow past the proximal head. Optionally, the sheath is configured to operatively couple with another device. Optionally, the sheath may be further attached to an external pump.

Figure 32:
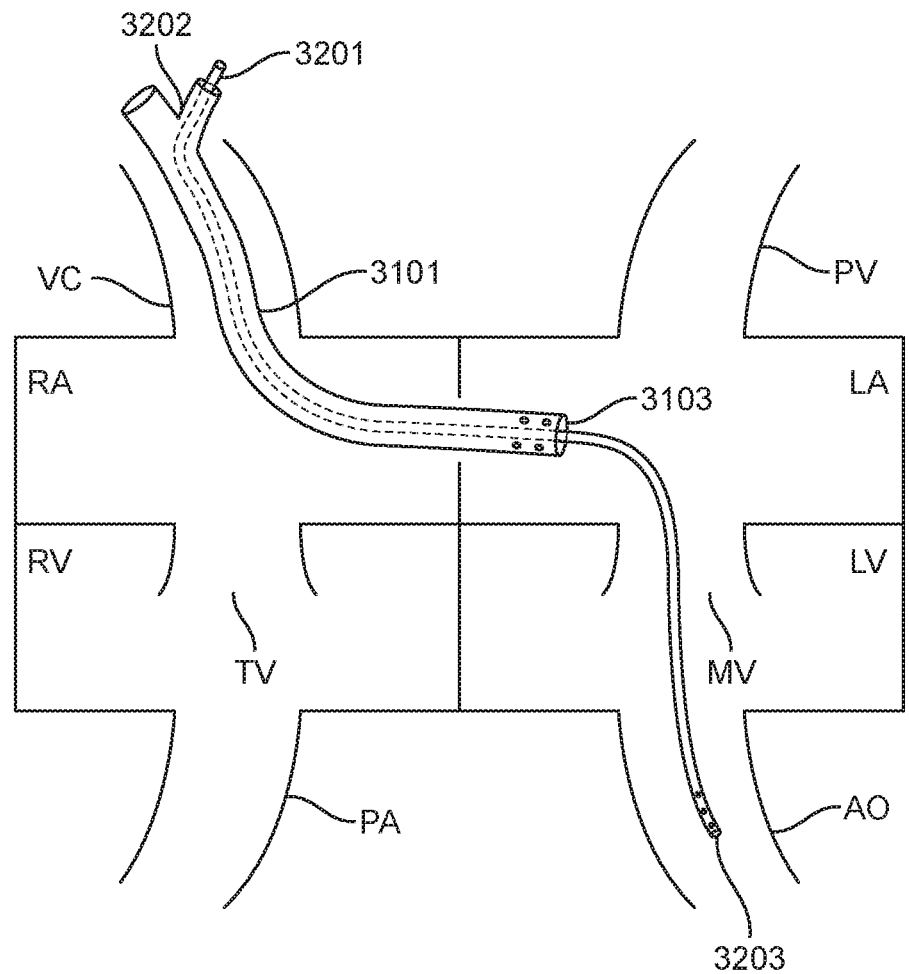
FIG. 32 illustrates an exemplary embodiment of a catheter disposed in a sheath in the heart.

FIG. 32 illustrates an exemplary embodiment of a second catheter 3201 inserted into a proximal head 3202 of a sheath 3101, slideably disposed in the sheath 3101, and exiting out of the distal tip 3103 and the distal portion of the catheter 3203 disposed in the aorta AO. Optionally, blood is removed from the sheath. Optionally, blood is returned to the second catheter. Optionally, the sheath is configured to deliver the second catheter through the one or more proximal heads of the sheath.

Figure 33A:
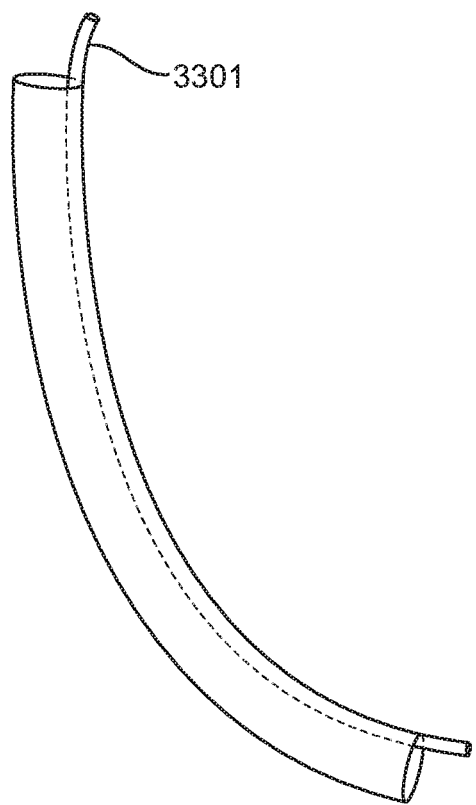
FIGS. 33A-33B illustrate exemplary embodiments of an outlet catheter.
Figure 33B:
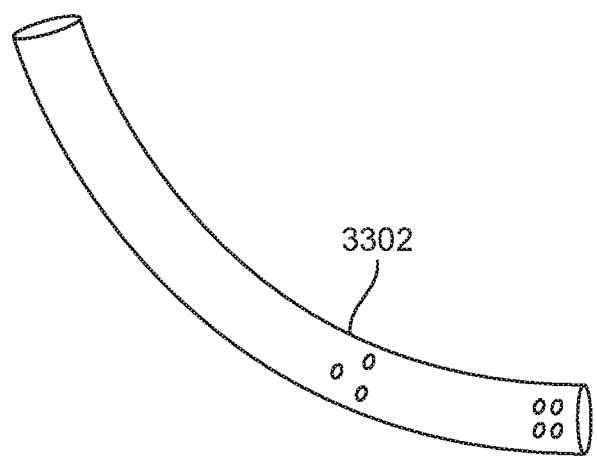

FIGS. 33A-33B illustrate exemplary embodiments of an outlet catheter. In some embodiments, the outlet catheter comprises an additional lumen 3301. In other embodiments, the outlet catheter comprises additional ports 3302 to deliver blood to the left ventricle, the left atrium, or both.

Figure 34A:
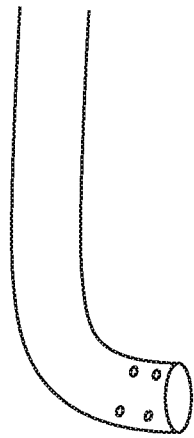
FIGS. 34A-34D illustrate exemplary embodiments of a pre-curvature catheter.
Figure 34B:
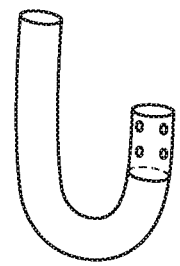
Figure 34C:
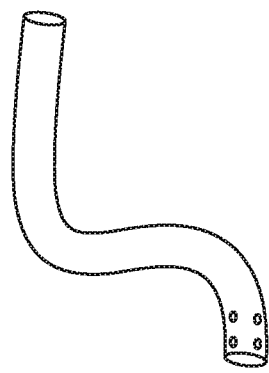
Figure 34D:
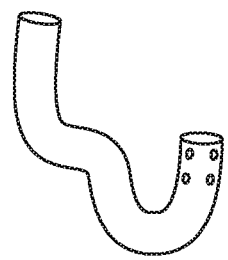

FIGS. 34A-34D illustrate exemplary embodiments of a pre-curvature catheter. FIG. 34A illustrates an exemplary embodiment of a pre-curved catheter to introduce into the left atrium. FIG. 34B illustrates an exemplary embodiment of a pre-curved catheter to be introduced into the aorta from the internal jugular vein (IJV). FIG. 34C illustrates an exemplary embodiment of a pre-curved catheter to be introduced into the left ventricle from the internal jugular vein (IJV). FIG. 34D illustrates an exemplary embodiment of a pre-curved catheter to be introduced from the internal jugular vein (IJV) to the aorta.

Figure 35A:
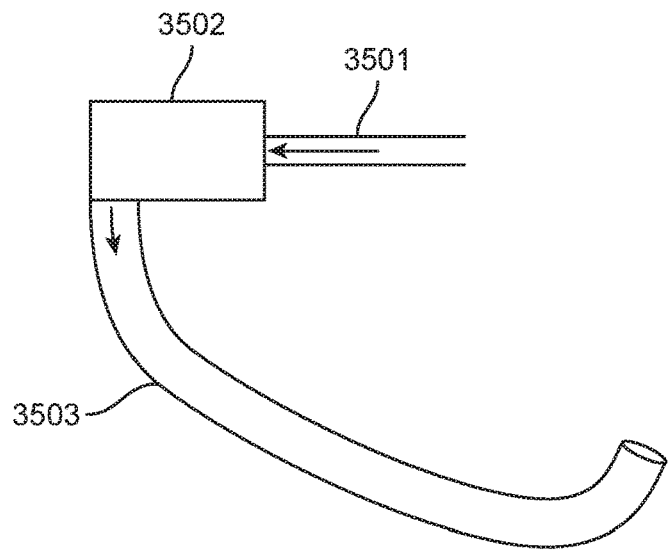
FIGS. 35A-35B illustrate exemplary embodiments of a hemodynamic support system.
Figure 35B:
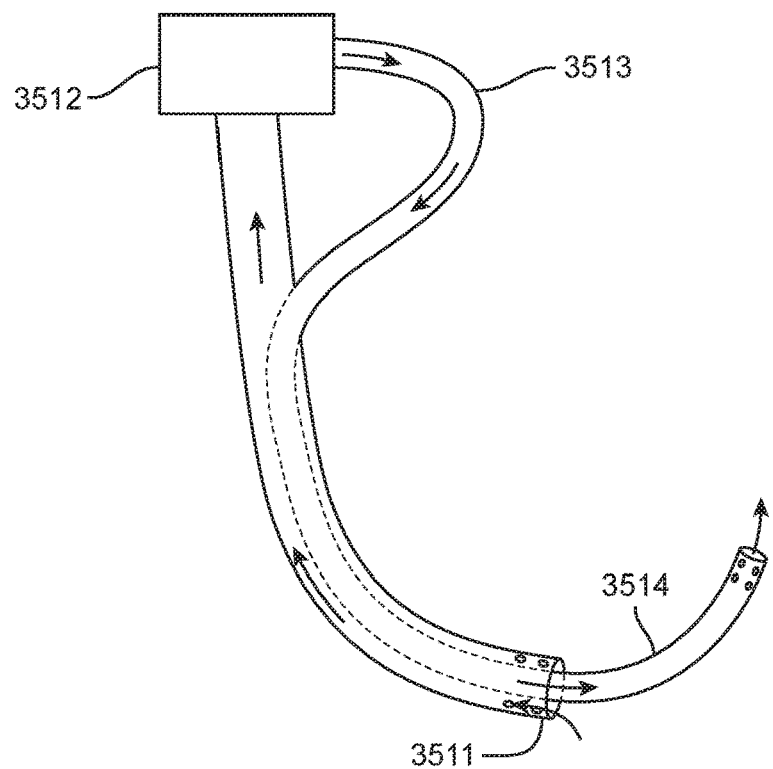

FIGS. 35A-35B illustrate exemplary embodiments of a hemodynamic support system. FIG. 35A illustrates a hemodynamic support system utilizing two separate catheters and a pump 3502. In some embodiments, a first catheter 3501 pumps blood from the heart to the pump 3502. In further embodiments, a distal portion of the first catheter 3501 is disposed in the left atrium, left ventricle, pulmonary artery, anywhere in the venous system, or anywhere in the right heart. In even further embodiments, the first catheter 3501 pumps blood from the left atrium, left ventricle, pulmonary artery, anywhere in the in the venous system, or anywhere in the right heart to the pump 3502. Optionally, in this and other embodiments, the pumped blood travels from the pump 3502 back through the second catheter 3503 back to the heart. In some embodiments, a distal portion of the second catheter 3503 is disposed in the aorta or the ascending aorta. In further embodiments, the blood travels from the second catheter 3503 to the aorta or the ascending aorta. Optionally, in some embodiments, the first catheter 3501 and the second catheter 3502 may comprise a plurality of apertures at the distal portion. Optionally, in other embodiments, the first catheter 3501 and the second catheter 3502 may comprise one single hole at the distal end and no plurality of apertures at the distal portion. In some embodiments, the pump 3502 is disposed outside of a body. FIG. 35B illustrates a hemodynamic support system utilizing an inner catheter 3513, an outer catheter 3511, and a pump 3512. In some embodiments, the outer catheter 3511 pumps blood from the heart to the pump 3512. In further embodiments, a distal portion of the outer catheter 3511 is disposed in the left atrium, left ventricle, pulmonary artery, anywhere in the venous system, or anywhere in the right heart. In even further embodiments, the outer catheter 3511 pumps blood from the left atrium, left ventricle, pulmonary artery, anywhere in the in the venous system, or anywhere in the right heart to the pump 3512. Optionally, in this and other embodiments, the pumped blood travels from the pump 3512 back through the inner catheter 3513 back to the heart. Optionally, in this and other embodiments, the pumped blood travels through the inner catheter 3513, parts of which is disposed within the outer catheter 3511. In some embodiments, a distal portion of the inner catheter 3514 is disposed in the aorta or the ascending aorta. In further embodiments, the blood travels from the inner catheter 3513 to the aorta or the ascending aorta. Optionally, in some embodiments, the outer catheter 3511 and the inner catheter 3513 may comprise a plurality of apertures at the distal portion. Optionally, in other embodiments, the outer catheter 3511 and the inner catheter 3513 may comprise one single hole at the distal end and no plurality of apertures at the distal portion. In some embodiments, the pump 3512 is disposed outside of a body.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of providing hemodynamic support to a patient's heart for alleviating workload therefrom, said method comprising:
   providing a hemodynamic support system, wherein the hemodynamic support system comprises a catheter, the catheter comprising at least two lumens and having an inlet port and outlet port, wherein the inlet port is proximal of the outlet port;
   introducing the catheter into a vein of the patient;
   advancing the catheter in an antegrade direction into a vena cava;
   advancing the catheter in the antegrade direction into a right atrium;
   passing the catheter transseptally from the right atrium into a left atrium;
   advancing the catheter across a mitral valve;
   advancing the catheter in the antegrade direction through a left ventricular outflow tract into an ascending aorta;
   removing blood from the patient via the inlet port and through a first of the at least two lumens and delivering the blood to another portion of the hemodynamic support system;
   returning the blood to the patient by delivering the blood through a second of the at least two lumens, wherein the blood is returned from the outlet port to the ascending aorta, the outlet port adjacent a distal portion of the catheter; and
   alleviating the workload on the patient's heart and supporting the patient's normal body functions.

2. The method of claim 1, wherein introducing the catheter into the vein of the patient comprises introducing the catheter into an internal jugular vein or a subclavian vein, thereby permitting increased patient mobility.

3. The method of claim 1, wherein passing the catheter transseptally from the right atrium into the left atrium comprises using a peel away sheath to access the left atrium.

4. A method of delivering hemodynamic support to a patient's heart for alleviating workload therefrom, said method comprising:
   providing a hemodynamic support system, wherein the hemodynamic support system comprises an outer catheter and an inner catheter, wherein the outer catheter comprises a first port, a second port, and a third port, wherein the inner catheter comprises an outlet port disposed on a distal portion thereof;
introducing the outer catheter into a vein of the patient and advancing the outer catheter towards the heart;
introducing the inner catheter into the first port;
advancing the inner catheter through the outer catheter in an antegrade direction and out the third port, wherein the third port is disposed on a distal portion of the outer catheter;
disposing the outlet port in an ascending aorta;
removing blood from the patient via the third port or a plurality of apertures disposed on the distal portion of the outer catheter, wherein the third port or the plurality of apertures is proximal of the outlet port;
moving the blood through the second port and delivering the blood to another portion of the hemodynamic support system;
returning the blood to the patient by delivering the blood through the outlet port; and
alleviating the workload on the patient's heart and supporting the patient's normal body functions.

5. The method of claim 4, wherein introducing the outer catheter into the vein of the patient comprises introducing the outer catheter into an internal jugular vein or a subclavian vein.

6. The method of claim 4, wherein introducing the inner catheter into the vein of the patient comprises introducing the inner catheter into an internal jugular vein or a subclavian vein.

7. The method of claim 4, wherein advancing the inner catheter in an antegrade direction further comprises:
advancing the inner catheter in an antegrade direction into a vena cava;
advancing the inner catheter in the antegrade direction into a right atrium;
passing the inner catheter transseptally from the right atrium into a left atrium;
advancing the inner catheter across a mitral valve; and
advancing the catheter in the antegrade direction through a left ventricular outflow tract into the ascending aorta.

8. The method of claim 7, wherein passing the inner catheter transseptally from the right atrium into the left atrium comprises using a peel away sheath to access the left atrium.

9. The method of claim 4, wherein the outer catheter comprises a plurality of axially oriented elongate elements disposed along the distal portion of the outer catheter, the method further comprising radially expanding the plurality of elongate elements thereby forming a barrier around the third port or the plurality of apertures, the barrier preventing tissue from obstructing the third port or the plurality of apertures, and further forming an anchor for the outer catheter.

10. The method of claim 4, wherein the third port or the plurality of apertures is disposed in the left atrium or the left ventricle.

11. A method of providing hemodynamic support to a patient's heart for alleviating workload therefrom, said method comprising:
providing a hemodynamic support system, wherein the hemodynamic support system comprises two separate catheters, an inlet catheter and an outlet catheter, the inlet catheter comprises an inlet port disposed on a distal portion thereof, the outlet catheter comprises an outlet port disposed on a distal portion thereof;
introducing the outlet catheter into a vein of the patient;
advancing the outlet catheter in an antegrade direction into an ascending aorta, wherein the outlet port is disposed in the ascending aorta;
introducing the inlet catheter into a vein of the patient;
advancing the inlet catheter proximal to the outlet port;
removing blood from the patient through the inlet catheter via the inlet port and delivering the blood to another portion of the hemodynamic support system;
returning the blood to the patient by delivering the blood to the ascending aorta through the outlet catheter via the outlet port; and
alleviating the workload on the patient's heart and supporting the patient's normal body functions.

12. The method of claim 11, wherein introducing the outlet catheter into the vein of the patient comprises introducing the catheter into an internal jugular vein or a subclavian vein, thereby permitting increased patient mobility.

13. The method of claim 11, wherein advancing the outlet catheter in an antegrade direction into an ascending aorta comprises:
advancing the outlet catheter in an antegrade direction into a vena cava
advancing the outlet catheter in the antegrade direction into a right atrium;
passing the outlet catheter transseptally from the right atrium into a left atrium;
advancing the outlet catheter across a mitral valve; and
advancing the outlet catheter in the antegrade direction through a left ventricular outflow tract into the ascending aorta.

14. The method of claim 13, wherein passing the outlet catheter transseptally from the right atrium into the left atrium comprises using a peel away sheath to access the left atrium.

15. The method of claim 11, wherein introducing the inlet catheter into the vein of the patient comprises introducing the catheter into an internal jugular vein or a subclavian vein, thereby permitting increased patient mobility.

16. The method of claim 11, wherein the inlet port is disposed in the left atrium, left ventricle, pulmonary artery, anywhere in a venous system of the patient, or anywhere in a right side of the heart.

17. The method of claim 11, wherein the inlet catheter comprises a plurality of axially oriented elongate elements disposed along the distal portion of the inlet catheter, the method further comprising radially expanding the plurality of elongate elements thereby forming a barrier around the inlet port or the plurality of apertures, the barrier preventing tissue from obstructing the inlet port or the plurality of apertures, and further forming an anchor for the inlet catheter.

18. A method of providing hemodynamic support to a patient's heart for alleviating workload therefrom, said method comprising:
providing a hemodynamic support system, wherein the hemodynamic support system comprises a catheter system, a second catheter, a snare, and a guide wire;
introducing the snare into an internal jugular vein or a subclavian vein of the patient;
advancing the snare into an inferior vena cava;
introducing the second catheter into a common femoral vein of the patient;
advancing the second catheter through the snare;
advancing the second catheter in an antegrade direction into a right atrium;
passing the second catheter transseptally from the right atrium into the left atrium;

advancing the second catheter across a mitral valve;

advancing the second catheter in the antegrade direction through a left ventricular outflow tract into an ascending aorta;

introducing the guide wire into the second catheter from the common femoral vein;

advancing the guide wire through the second catheter to the ascending aorta;

removing the second catheter from the patient while the guide wire remains in the patient;

snaring the guide wire with the snare;

externalizing the proximal portion of the guide wire from the internal jugular vein or the subclavian vein;

introducing the catheter system into the internal jugular vein or the subclavian vein; and advancing the catheter system into the heart, wherein a distal portion of the catheter system is positioned in the ascending aorta.

19. The method of claim 18, wherein the hemodynamic support system further comprises a second snare, wherein the second snare is introduced into an artery of the patient, wherein the second snare snares one portion of the guide wire.

20. The method of claim 19, wherein the one portion of the guide wire is externalized from a peripheral artery.

* * * * *

UNITED STATES PATENT AND TRADEMARK OFFICE
CERTIFICATE OF CORRECTION

PATENT NO. : 10,307,575 B2
APPLICATION NO. : 15/943477
DATED : June 4, 2019
INVENTOR(S) : Khaldoon Alaswad It is certified that error appears in the above-identified patent and that said Letters Patent is hereby corrected as shown below:

In the Claims

In Column 28, Line 22, in Claim 13, after "cava", insert --;--

Signed and Sealed this
Fourteenth Day of April, 2020

Andrei Iancu
*Director of the United States Patent and Trademark Office*